United States Patent
Lockhart et al.

(10) Patent No.: US 11,241,422 B2
(45) Date of Patent: *Feb. 8, 2022

(54) METHODS FOR TREATMENT OF FABRY DISEASE

(71) Applicant: Amicus Therapeutics, Inc., Cranbury, NJ (US)

(72) Inventors: David J. Lockhart, Emerald Hills, CA (US); Jeff Castelli, New Hope, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 38 days.

This patent is subject to a terminal disclaimer.

(21) Appl. No.: 16/564,694

(22) Filed: Sep. 9, 2019

(65) Prior Publication Data

US 2019/0388409 A1 Dec. 26, 2019

Related U.S. Application Data

(60) Continuation of application No. 15/974,222, filed on May 8, 2018, now Pat. No. 10,406,143, which is a continuation of application No. 15/338,923, filed on Oct. 31, 2016, now Pat. No. 9,987,263, which is a continuation of application No. 14/641,707, filed on Mar. 9, 2015, now Pat. No. 9,480,682, which is a continuation of application No. 13/445,338, filed on Apr. 12, 2012, now Pat. No. 9,000,011, which is a continuation of application No. 12/966,904, filed on Dec. 13, 2010, now abandoned, which is a division of application No. 11/749,512, filed on May 16, 2007, now Pat. No. 7,851,143.

(60) Provisional application No. 60/853,631, filed on Oct. 23, 2006, provisional application No. 60/801,089, filed on May 16, 2006.

(51) Int. Cl.

| | |
|---|---|
| *A61K 31/445* | (2006.01) |
| *A61K 31/45* | (2006.01) |
| *A61K 45/06* | (2006.01) |
| *C07D 211/46* | (2006.01) |
| *G01N 33/50* | (2006.01) |
| *A61K 9/00* | (2006.01) |
| *A61K 9/48* | (2006.01) |

(52) U.S. Cl.
CPC .......... *A61K 31/445* (2013.01); *A61K 9/0053* (2013.01); *A61K 9/48* (2013.01); *A61K 31/45* (2013.01); *A61K 45/06* (2013.01); *C07D 211/46* (2013.01); *G01N 33/5094* (2013.01); *G01N 2333/924* (2013.01); *G01N 2333/94* (2013.01); *G01N 2800/04* (2013.01); *G01N 2800/52* (2013.01)

(58) Field of Classification Search
CPC ...... A61K 31/445; A61K 9/48; A61K 9/0053; A61K 45/06; A61K 31/45; G01N 33/5094; G01N 2800/52; G01N 2800/04; G01N 2333/94; G01N 2333/924; C07D 211/46

See application file for complete search history.

(56) References Cited

U.S. PATENT DOCUMENTS

| | | |
|---|---|---|
| 5,900,360 A | 5/1999 | Welch et al. |
| 6,270,954 B1 | 8/2001 | Welch et al. |
| 6,274,597 B1 * | 8/2001 | Fan ..................... A61K 31/445 514/315 |
| 6,541,195 B2 | 4/2003 | Welch et al. |
| 6,583,158 B1 | 6/2003 | Fan et al. |
| 6,589,964 B2 | 7/2003 | Fan et al. |
| 6,599,919 B2 | 7/2003 | Fan et al. |
| 6,774,135 B2 | 8/2004 | Fan et al. |
| 6,916,829 B2 | 7/2005 | Fan et al. |
| 7,141,582 B2 | 11/2006 | Fan et al. |
| 7,622,485 B2 | 11/2009 | Fan et al. |
| 7,851,143 B2 | 12/2010 | Kaneski et al. |
| 7,973,157 B2 | 7/2011 | Major et al. |
| 8,321,148 B2 | 11/2012 | Lockhart et al. |
| 8,592,362 B2 | 11/2013 | Benjamin et al. |
| 9,000,011 B2 | 4/2015 | Lockhart et al. |
| 9,056,101 B2 | 6/2015 | Lockhart |
| 9,066,939 B2 | 6/2015 | Schiffmann et al. |
| 9,095,584 B2 | 8/2015 | Benjamin et al. |
| 9,181,184 B2 | 11/2015 | Mugrage et al. |
| 9,206,457 B2 | 12/2015 | Do |
| 9,480,682 B2 | 11/2016 | Lockhart et al. |
| 9,545,397 B2 | 1/2017 | Benjamin et al. |
| 9,694,056 B2 | 7/2017 | Khanna et al. |
| 9,987,263 B2 | 6/2018 | Lockhart et al. |
| 9,999,618 B2 | 6/2018 | Castelli et al. |
| 10,076,514 B2 | 9/2018 | Benjamin |

(Continued)

FOREIGN PATENT DOCUMENTS

| | | |
|---|---|---|
| AU | 2004289083 A1 | 5/2005 |
| CA | 2086413 A1 | 12/1991 |

(Continued)

OTHER PUBLICATIONS

U.S. Appl. No. 16/642,620, filed Feb. 27, 2020. "Methods Of Enhancing And/Or Stabilizing Cardiac Function In Patients With Fabry Disease".
U.S. Appl. No. 16/678,183, filed Nov. 8, 2019. "Methods Of Treating Fabry Patients Having Renal Impairment".
U.S. Appl. No. 16/744,884, filed Jan. 16, 2020. "Methods Of Treating Fabry Disease In Patients Having The G9331A Mutation In The GLA Gene".
U.S. Appl. No. 16/806,404, filed Mar. 2, 2020. "Dosing Regimens For The Treatment Of Fabry Disease".

(Continued)

*Primary Examiner* — Sahar Javanmard
(74) *Attorney, Agent, or Firm* — Servilla Whitney LLC

(57) ABSTRACT

Provided are in vitro and in vivo methods for determining whether a patient with Fabry disease will respond to treatment with a specific pharmacological chaperone.

16 Claims, 7 Drawing Sheets

(56) References Cited

U.S. PATENT DOCUMENTS

| | | |
|---|---|---|
| 10,155,027 B2 | 12/2018 | Khanna et al. |
| 10,251,873 B2 | 4/2019 | Castelli et al. |
| 10,357,548 B2 | 7/2019 | Khanna |
| 10,383,864 B2 | 8/2019 | Lockhart et al. |
| 10,406,143 B2 | 9/2019 | Lockhart et al. |
| 10,471,053 B2 | 11/2019 | Castelli et al. |
| 10,525,045 B2 | 1/2020 | Castelli et al. |
| 10,537,564 B2 | 6/2020 | Benjamin |
| 10,792,278 B2 | 10/2020 | Castelli et al. |
| 10,792,279 B2 | 10/2020 | Castelli et al. |
| 10,799,491 B2 | 10/2020 | Castelli et al. |
| 10,806,727 B2 | 10/2020 | Castelli et al. |
| 10,813,921 B2 | 10/2020 | Benjamin et al. |
| 10,849,889 B2 | 12/2020 | Castelli et al. |
| 10,849,890 B2 | 12/2020 | Castelli et al. |
| 10,857,141 B2 | 12/2020 | Castelli et al. |
| 10,857,142 B2 | 12/2020 | Castelli et al. |
| 10,874,655 B2 | 12/2020 | Castelli et al. |
| 10,874,656 B2 | 12/2020 | Castelli et al. |
| 10,874,657 B2 | 12/2020 | Castelli et al. |
| 10,925,866 B2 | 2/2021 | Castelli et al. |
| 2004/0180419 A1 | 9/2004 | Fan |
| 2005/0137223 A1 | 6/2005 | Fan et al. |
| 2005/0203019 A1 | 9/2005 | Conn |
| 2006/0264467 A1 | 11/2006 | Mugrage et al. |
| 2006/0287358 A1 | 12/2006 | Wustman |
| 2007/0021381 A1 | 1/2007 | Fan et al. |
| 2007/0270486 A1 | 11/2007 | Kopito et al. |
| 2010/0004156 A1 | 1/2010 | Kaushal et al. |
| 2011/0152319 A1 | 6/2011 | Banjamin et al. |
| 2011/0212996 A1 | 9/2011 | Banjamin et al. |
| 2018/0153999 A1 | 6/2018 | Greene et al. |
| 2018/0360812 A1 | 12/2018 | Castelli et al. |
| 2018/0360814 A1 | 12/2018 | Castelli et al. |
| 2019/0000818 A1 | 1/2019 | Benjamin et al. |
| 2019/0183869 A1 | 6/2019 | Castelli |
| 2019/0358302 A1 | 11/2019 | Goteschall |
| 2019/0388409 A1 | 12/2019 | Lockhart et al. |
| 2020/0215043 A1 | 7/2020 | Benjamin |
| 2020/0222377 A1 | 7/2020 | Castelli et al. |
| 2020/0268890 A1 | 8/2020 | Greene et al. |
| 2021/0030730 A1 | 2/2021 | Castelli et al. |
| 2021/0038579 A1 | 2/2021 | Barth et al. |
| 2021/0038581 A1 | 2/2021 | Castelli et al. |
| 2021/0038582 A1 | 2/2021 | Castelli et al. |
| 2021/0038583 A1 | 2/2021 | Castelli et al. |
| 2021/0038624 A1 | 2/2021 | Barth |
| 2021/0038625 A1 | 2/2021 | Benjamin et al. |

FOREIGN PATENT DOCUMENTS

| | | |
|---|---|---|
| JP | 2003-528799 A | 9/2003 |
| WO | 1990011353 A1 | 10/1990 |
| WO | 9200277 A1 | 1/1992 |
| WO | 99/62517 A1 | 12/1999 |
| WO | 2004074450 A2 | 9/2004 |
| WO | 2004/103368 A1 | 12/2004 |
| WO | 2006/125141 A2 | 11/2006 |
| WO | 2007/137072 A2 | 11/2007 |
| WO | 2008045015 A1 | 4/2008 |
| WO | 2008/121826 A2 | 10/2008 |
| WO | 2008134628 A2 | 11/2008 |
| WO | 2009102895 A3 | 8/2009 |
| WO | 2010048532 A1 | 4/2010 |
| WO | 2010138608 A1 | 12/2010 |
| WO | 2011063048 A2 | 5/2011 |
| WO | 2012071451 A2 | 5/2012 |
| WO | 2012125402 A3 | 9/2012 |
| WO | 2014014938 A1 | 1/2014 |
| WO | 2017165164 A1 | 9/2017 |
| WO | 2018017721 A1 | 1/2018 |
| WO | 2018132471 A1 | 7/2018 |
| WO | 2018222655 A1 | 12/2018 |
| WO | 2019017938 A1 | 1/2019 |
| WO | 2019046244 A1 | 3/2019 |
| WO | 2019157047 A1 | 8/2019 |
| WO | 2019157056 A1 | 8/2019 |
| WO | 2020040806 A1 | 2/2020 |
| WO | 2020252129 A1 | 12/2020 |
| WO | 2021026447 A1 | 2/2021 |

OTHER PUBLICATIONS

U.S. Appl. No. 16/817,877, filed Mar. 13, 2020. "Methods Of Treating Fabry Patients Having Renal Impairment".
U.S. Appl. No. 16/817,881, filed Mar. 13, 2020. "Methods Of Treating Fabry Patients Having Renal Impairment".
U.S. Appl. No. 16/817,888, filed Mar. 13, 2020. "Methods Of Treating Fabry Patients Having Renal Impairment".
U.S. Appl. No. 16/817,895, filed Mar. 13, 2020. "Methods Of Treating Fabry Patients Having Renal Impairment".
U.S. Appl. No. 16/817,900, filed Mar. 13, 2020. "Methods Of Treating Fabry Patients Having Renal Impairment".
U.S. Appl. No. 16/817,908, filed Mar. 13, 2020. "Methods Of Treating Fabry Patients Having Renal Impairment".
U.S. Appl. No. 16/817,911, filed Mar. 13, 2020. "Methods Of Treating Fabry Patients Having Renal Impairment".
U.S. Appl. No. 16/817,918, filed Mar. 13, 2020. "Methods Of Treating Fabry Patients Having Renal Impairment".
U.S. Appl. No. 16/817,925, filed Mar. 13, 2020. "Methods Of Treating Fabry Patients Having Renal Impairment".
U.S. Appl. No. 16/817,927, filed Mar. 13, 2020. "Methods Of Treating Fabry Patients Having Renal Impairment".
U.S. Appl. No. 17/076,336, filed Oct. 21, 2020. "Methods Of Treating Fabry Patients Having Renal Impairment".
U.S. Appl. No. 17/076,340, filed Oct. 21, 2020. "Methods Of Treating Fabry Patients Having Renal Impairment".
U.S. Appl. No. 17/077,393, filed Oct. 22, 2020. "Methods Of Treating Fabry Patients Having Renal Impairment".
U.S. Appl. No. 17/077,402, filed Oct. 22, 2020. "Methods Of Treating Fabry Patients Having Renal Impairment".
U.S. Appl. No. 17/079,859, filed Oct. 26, 2020. "Method To Predict Response To Pharmacological Chaperone Treatment Of Diseases".
U.S. Appl. No. 17/148,817, filed Jan. 14, 2021. "Highly Purified Batches Of Pharmaceutical Grade Migalastat And Methods Of Producing The Same".
U.S. Appl. No. 17/172,846, filed Feb. 10, 2021. "Methods Of Treating Fabry Disease".
Alfonso, et al., "Miglustat (NB-DNJ) works as a chaperone for mutated acid betaglucosidase in cells transfected with several Gaucher disease mutations", Blood cells, Molecules and Diseases, 35(2), 2005, 268-276.
Andersson, Hans C., et al., "Individualization of Long-Term Enzyme Replacement Therapy for Gaucher Disease", Genetics in Medicine, 2005, vol. 7, No. 2, pp. 105-110.
Bishop, et al., "Human Alpha-Galactosidase A: Nucleotide Seqence of a cDNA Clone Encoding the Mature Enzyme", Proc. Natl. Acad. Sci. USA vol. 83, 1986, 4859-4863.
Bishop, et al., "Molecular Genetics", Am. J. Hum. Genet. vol. 37, 1985, p. A144.
Brady, et al., "Enzymatic Defect in Fabry's Disease. Ceramidetrihexosidase Deficiency", N. Engl. J. Med. vol. 276, 1967, 1163-1167.
Branum, et al., "Effect of Two Anticoagulants on Leukocyte Yield and Function, and on Lysosomal Enzyme Activity", Clin. Chem. vol. 34 No. 1, 1988, 110-113.
Brooks, "Getting into the fold", Nature Chemical Biology vol. 3 No. 2, Feb. 2007, 84-85.
Brown, et al., "Strategies for Correction the Delta F508 CFTR Protein-Folding Defect", Journal of Bioenergetics and Biomembranes vol. 29 No. 5, 1997, 491-502.
Butters, T. D., "Expert Opin. Pharmacother., 2007, vol. 8, No. 4,, pp. 427-435".
Calhoun, et al., "Fabry Disease: Isolation of a cDNA Clone Encoding Human Apha-Calactosidase A", Proc. Natl. Acad. Sci. USA vol. 82, 1985, 7364-7368.

(56) References Cited

OTHER PUBLICATIONS

Choi, Sung Won, et al., "Mutant Tamm-Horsfall Glycoprotein Accumulation in Endoplasmic Reticulum Induces Apoptosis Reversed by Colchicine and Sodium 4-Phenylbutyrate", J Am Soc Nephrol 16: 3006-3014, 2005.
Davies, et al., "Fabry Disease: Fourteen Alpha-Galactosidase A Mutations in Unrelated Families From the United Kingdom and Other European Countries", Eur. J. Hum. Genet. vol. 4, 1996, 219-224.
Desnick, et al., "Metabolic and Molecular Bases of Inherited Disease", Scriver, et al. (eds.) 8th ed., Graw-Hill, New York, 2001, 3733-3774.
Dobrovolny, Robert, et al., ""Relationship between X-inactivation and clinical involvement in Fabry heterozygotes. Eleven novel mutations in the [alpha]-galactosidase A gene in the Czech and Slovak population",", 8/1/205, 647-654.
Eng, et al., "Fabry Disease: Thirty-Five Mutations in the Alpha-Galactosidase A Gene in Patients with Classic and Variant Phenotypes", Mol. Med. vol. 3, 1997, 174-182.
Eng, et al., "Nature and Frequency of Mutations in the Alpha-Galactosidase A Gene That Cause Fabry Disease", Am. J. Hum. Genet. vol. 53, 1993, 1186-1197.
Fan, Jian-Qiang, et al., "A contradictory treatment for lysosomal storage disorders: inhibitors enhance mutant enzyme activity", TRENDS in Pharm. Sci. vol. 24 No. 7, Jul. 2003, 355-360.
Fan, Jian-Qiang, et al., "Accelerated transport and maturation of lysosomal alpha-galactosidase A in Fabry Tymphoblasts by an enzyme inhibitor", Nat. Med. vol. 5 No. 1, 1999, 112-115.
Fan, et al., "Cell-based screening of active-site specific chaperone for the treatment of 5. Fabry disease", Methods in Enzymology, 363: 412-420 (2003).
Flanagan, et al., "The pharmacological chaperone 1-deoxynojirimycin increases the activity and lysosomal trafficking of multiple mutant forms of acid alpha-glucosidase", Human Mutation 30: 1683-1692., 2009.
Frustaci, Andrea, et al., "Improvement in Cardiac Function in the Cardiac Variant of Fabry's Diseas with Galactose-Infusion Therapy", New England Journal of Medicine, vol. 345, No. 1, Jul. 5, 2001, 25-32.
Fuller, et al., "Urinary Lipid Profiling for the Identification of Fabry Hemizygotes and Heterozygotes", Clinical Chemistry vol. 51, 2005, 688-694.
Garman, Scott C., et al., "Structure-function relationships in α-galactosidase A", Structure-function relationships in α-galactosidase A.
Germain, Dominique P., et al., "Fabry Disease: Twenty Novel Alpha-Galactosidase A Mutations and Genotype-Phenotype Correlations in Classical and Variant Phenotypes", Molecular Medicine 8(6): 306-312, 2002, May 15, 2002.
Germain, Dominique P., et al., "Safety and pharmacodnamic effects of a pharmacological chaperone on a-galactosidase A activity and globotriaosylceramide clearance in Fabry disease: report from two phase 2 clinical studies", Journal of Rare Diseases 7:91, 2012, 11 pgs.
Germain, Dominique P., et al., "Treatment of Fabry's Disease with the Pharmacologic Chaperone Migalastat", N Engl J Med 2016;375:545-55., Aug. 11, 2016.
Giugliani, R., et al., "A Phase 2 study of migalastat hydrochloride in females with Fabry disease: Selection of population, safety and pharmacodynamic effects", Molecular Genetics and Metabolism 109, 2013, 86-92.
EU Clinical Trials Register, Feb. 13, 2006, https://www.clinicaltrialsregister.eu/ctr-search/trial/2006-000181-36/GB, 1-4.
EU Clinical Trials Register, Oct. 17, 2005, https://www.clinicaltrialsregister.eu/ctr-search/trial/2005-004384-33/GB, 1-4.
NCT00214500 on Sep. 21, 2005: https://clinicaltrials.gov/archive/NCT00214500/2005_09_21, Sep. 21, 2005, https://clinicaltrials.gov/archive/NCT00214500/2005_09_21, 1-3.
NCT00283959 on Jul. 30, 2006: ClinicalTrials.gov Archive, Jan. 30, 2006, https://clinicaltrials.gov/archive/NCT00283959/2006_01_30, 1-3.
NCT00304512 on Mar. 17, 2006: ClinicalTrials.gov Archive, Mar. 17, 2006, https://clinicaltrials.gov/archive/NCT00304512/2006_03_17, 1-4.
"Sakuraba, 2010 at fabry-database.org/mutants."
""The pharmacological chaperone 1-deoxygal actonoj i rimyci n increases !+—galactosidase A levels in Fabry patient cell lines",", Journal of Inherited Metabolic Disease, Kluwer Academic Publishers, DO, vol. 32, No. 3,, Apr. 18, 2009, 424-440.
"•NCT00283933 on Jan. 30, 2006: ClinicalTrials.gov Archive, Jan. 30, 2006, https://clinicaltrials.gov/archive/NCT00283933/2006_01_30, 1-3."
"A Phase 2, Open-Label, Multicenter, Ascending-Dose, 12-Week Study to Evaluate the Safety, Tolerability, Pharmacokinetics, and Pharmacodynamics of AT1001 in Patients with Fabry Disease", ClinicalTrials.gov Archive, Sep. 21, 2005.
"A Phase 2, Open-Label, Multiple Dose Level, 12-Week Study to Evaluate the Safety, Tolerability, and Pharmacodynamics of AT1001 in Female Patients With Fabry Disease", ClinicalTrials.gov Archive, Mar. 17, 2006.
"A Phase 2, Open-Label, Multiple Dose Level, 12-Week Study to Evaluate the Safety, Tolerability, and Pharmacodynamics of AT1001 in Female Patients with Fabry Disease", EU Clinical Trials Register, Feb. 13, 2013.
"A Phase 2, Open-Label, Single Dose Level, 12-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients With Fabry Disease", ClinicalTrials.gov Archive, Jan. 30, 2006.
"A Phase 2, Open-Label, Single Dose Level, 24-Week Study to Evaluate the Safety, Tolerability, and Pharmacodynamics of AT1001 in Patients with Fabry Disease", EU Clinical Trials Register, Oct. 17, 2005.
"Amicus Therapeutics Announces Positive Phase 3 Data From Fabry Monotherapy Study 012", Aug. 20, 2014.
Extended European Search Report for EP 08 74 7020 dated Sep. 30, 2010, 3 pages.
Final Office Action in U.S. Appl. No. 11/749,512, dated Jun. 16, 2010, 13 pages.
Final Office Action in U.S. Appl. No. 12/966,904, dated Jan. 12, 2012, 10 pages.
Final Office Action in U.S. Appl. No. 13/445,338, dated Sep. 11, 2013, 9 pages.
GALAFOLD Label (2018).
GALAFOLD Product Information.
Galafold Summary of Product Characteristics, May 2016, 45 pgs.
GALAFOLD U.S. Label, Revised Aug. 10, 2018, 24 pages.
Non-Final Office Action in U.S. Appl. No. 11/749,512, dated Nov. 18, 2009, 10 pages.
Non-Final Office Action in U.S. Appl. No. 12/966,904, dated May 17, 2011, 11 pages.
Non-Final Office Action in U.S. Appl. No. 13/445,338, dated Feb. 5, 2013, 7 pages.
Non-Final Office Action in U.S. Appl. No. 15/974,217, dated Dec. 13, 20018, 18 pages.
Non-Final Office Action in U.S. Appl. No. 12/855,468 dated Apr. 27, 2012,13 pages.
Non-Final Office Action in U.S. Appl. No. 12/860,611 dated Apr. 27, 2012.
Non-Final Office Action in U.S. Appl. No. 14/713,821 dated Mar. 15, 2016, 10 pages.
Non-Final Office Action in U.S. Appl. No. 15/338,923 dated Nov. 15, 2017, 9 pages.
Non-Final Office Action in U.S. Appl. No. 15/974,222 dated Aug. 10, 2018, 11 pages.
Non-Final Office Action in U.S. Appl. No. 16/222,305, dated Jul. 24, 2020, 7 pages.

(56) References Cited

OTHER PUBLICATIONS

PCT Application No. PCT/US20/14531; Filed Jan. 22, 2020. "Methods of Reducing Cerebrovascular Events in Patients With Fabry Disease".
PCT Application No. PCT/US21/17446; Filed Feb. 10, 2021. "Methods Of Treating Fabry Disease".
PCT International Search Report for PCT/US08/61764 dated Oct. 7, 2008, 2 pages.
PCT International Search Report in PCT/US2009/033963 dated Oct. 22, 2009, 3 pages.
Phase I Clinical Studies Demonstrate Safety and Initial "Proof of Concept" for Amicus' Fabry Disease Drug.
"QIAGEN Supplementary Protocol: Fast-forward protocol for transient transfection of 293 cells in 96-well plates using effectene transfection reageny", Nov. 1, 2006, retrieved from the Internet: URL:www.qiagen.com, [retrieved on Jun. 21, 2012].
"QIAGEN Supplementary Protocol: Transient transfection of 293 cells in 96-well plates using Polyfect Transfection Reagent", Aug. 1, 2001, retrieved from the Internet: URL:www.qiagen.com [retrieved on Jun. 21, 2012].
"QIAGEN Supplementary Protocol: Transient transfection of COS-7 cells in 96-well plates using Polyfect Transfection Reagent", retrieved from the Internet URL:www.qiagen, com/literature/render.aspx?id=543 [retrieved on Jun. 21, 2012].
Supplemental European Search Report in EP 07797506.8, dated Feb. 15, 2010.
Supplemental European Search Report in EP 08747020.9, dated Aug. 10, 2010.
"Transfecting Plasmid DNA into COS-7 Cells Using Lipofectamine (TM) LTX Reagent", Jun. 9, 2006, retrieved from the Internet: URL:www.invitrogen,com [retrieved on Jun. 21, 2012].
"Transfecting Plasmid DNA into GripTite (TM) 293 MSR Cells Using Lipofectamine (TM) LTX Reagent", Jan. 1, 2006, retrieved from the Internet URL:htp://www.invitrogen.com/etc/medialib/en/filelibrary/pdf/protocols.Par.I8853.File.dat/Human embryonic kidney.pdf, [retrieved on Jun. 21, 2012].
"Transfecting Plasmid DNA into HEK293 Cells Using Lipofectamine (TM) LTX Reagent", Jan. 1, 2006, retrieved from the Internet: URL:www.invitrogen.com. [retrieved on Jun. 21, 2012].
U.S. Appl. No. 16/046,247, filed Jul. 26, 2018. "Method To Predict Response To Pharmacological Chaperon Treatment Of Diseases".
U.S. Appl. No. 16/222,305, filed Dec. 17, 2018. "Method To Predict Response To Pharmacological Chaperone Treatment Of Diseases".
Ishii , et al., "Aggregation of the Inactive Form of Human alpha-Galactosidase in the Endoplasmic Reticulum", Biochem. Biophys. Res. Comm. vol. 220, 1996, 813-815.
Ishii , et al., "Mutant a-galactosidase A enzymes identified in Fabry disease patients with residual enzyme activity: biochemical characterization and restoration of normal intracellular processing by 1-deoxygalactonorjirimycin", Biochemi J. 406(2): 285-295., Sep. 1, 2007.
Ishii, Satoshi , et al., "Role of Ser-65 in the activity of a-galactosidase A: characterization of a point mutation (S65T) detected in a patient with Fabry disease", Archives of biochemistry and biophysics, 377(2), May 15, 2000 (May 15, 2000).
Ishii , et al., "Transgenic mouse expressing human mutant alpha-Galactosidase A in an endogenous enzyme deficienct background: a biochemical animal model for studying active-site specific chaperone therapy for Fabry disease", Biochem et Biophysica Acta vol. 1690, 2004, 250-257.
Kornreich , et al., "Nucleotide Sequence of the Human Alpha-Galactosidase A Gene", Nucleic Acids Res. vol. 17, 1989, 3301-3302.
Kusiak , et al., "Purification and Properties of the Two Major Isozymes of Apha-Galactosidase from Human Placenta", J. Biol. Chem. Vo. 253, 1978, 184-190.
Lei , et al., "Enzyme enhancement activity of N-octyl-beta-valienamine on betaglucosidase in cells transfected with several Gaucher disease mutations", Biochimica et Biophysica Acta. Molecular Basis ofDisease, 1772(5):587-596 (2007).

Matsuzawa, Fumiko , et al., ""Fabry disease: correlation between structural changes in [alpha]-galactosidase, and clinical and biochemical phenotypes",", Human Genetics, Springer, Berlin, DE, vol. 117, No. 4, Aug. 1, 2005, 317-328.
Mayes , et al., "Differential Assay for Lysosomal Alpha-Galactosidases in Human Tissues and its Application to Fabry's Diesease", Clin. Chim. Acta vol. 112 No. 2, 1981, 247-251.
Mignani, Renzo , et al., "Agalsidase therapy in patients with Fabry disease on renal replacement therapy: a nationwide study in Italy", Nephrol Dial Transplant (2008) 23: 1628-1635, Dec. 5, 2007.
Nakao , et al., "An Atypical Variant of Fabry's Disease in Men with Left Ventricular Hypertrophy", N. Engl. J. Med. vol. 333, 1995, 288-293.
Park , et al., "Long-Term Correction of Globotriaosylceramide Storage in Fabry Mice by Recombinant Adeno-Associated Virus-Mediated Gene Transfer", Proc. Natl. Acad. Sci. USA vol. 100, 2003, 3450-3454.
Ron, Idit , et al., "ER retention and degradation as the molecular basis underlying Gaucher disease heterogeneity", Human Molecular Genetics, 2005, vol. 14, No. 16, Jul. 6, 2005, 2387-2398.
Sawkar, Anu R. , et al., "Gaucher Disease-Associated Glucocerebrosidases Show Mutation-Dependent Chemical Chaperoning Profiles", Chemistry & Biology, vol. 12, Nov. 2005, 1235-1244.
Sawkar, A. R., et al., "Therapeutic Strategies to Ameliorate Lysosomal Storage Disorders—A Focus on Gaucher Disease", Cell. Mol. Life Sci. 63 (2006), pp. 1179-1192.
Shabbeer, Junaid , et al., "Fabry disease: 45 novel mutations in the a-galactosidase A gene causing the classical phenotype", Molecular Genetics and Metabolism 76 (2002) 23-30, Feb. 28, 2002.
Shabbeer, Junaid , et al., "Fabry disease: Identification of 50 novel a-galactosidase A mutations causing the classic phenotype and three-dimensional structural analysis of 29 missense mutations", Human Genomics. vol 2. No. 5. 297-309 Mar. 2006.
Shimotori , et al., "Novel mutations of the GLA gene in Japanese patients with fabry disease and their functional characterization by active site specification chaperone", Human Mutaion, 29(2): 331 (2008).
Shin, Sang H, et al., "Prediction of Response of Mutated alpha-Galactosidase A to a Pharmacological Chaperone", Pharmacogenet Genomics, vol. 18, No. 9, Sep. 2008, 773-780.
Shin, S , et al., "Screening for Pharmacological Chaperones in Fabry Disease", Materials and Methods vol. 359, 2007, 168-173.
Spada, Marco , et al., "High Incidence of Later-Onset Fabry Disease Revealed by Newborn Screening", The American Journal of Human Genetics vol. 79 Jul. 2006.
Steet , et al., "The iminosugar isofagomine increases the activity of N370S mutant acid beta-glucosidase in Gaucher fibroblasis by several mechanisms", PNAS vol. 103 No. 37, 2006, 13813-13818.
Thomas, Philip , et al., "HEK293 cell line: A vehicle for the expression of recombinant proteins (Abstract)", Journal of Pharmacological and Toxicological Methods, vol. 51, Issue 3, May-Jun. 2005, pp. 187-200.
Tokshika, Okumiya , et al., "Galactose stabilizes various missense mutants of alpha-galactosidase in Fabry disease", Biochemical and Biophysical Research Communications, Elsevier, Amsterdam, NL, vol. 214, No. 3,, Jan. 1, 1995, 1219-1224.
Topaloglu, Ali K., et al., "Twenty Novel Mutations in the a-Galactosidase A Gene Causing Fabry Disease", Molecular Medicine 5: 806-811, 1999, Oct. 27, 1999.
Toshika, Okumiya , et al., "Galactose stabilizes various missense mutants of alpha-galactosidase in Fabry disease", Biochemical and Biophysical Research Communications, Elsevier, Amsterdam, NL, vol. 214, No. 3,, Jan. 1, 1995, 1219-1224.
Tsuji , et al., "Signal Sequence and DNA-Mediated Expression of Human Lysosomal Alpha-Galactosidase A", Eur. J. Biochem. vol. 165, 1987, 275-280.
Wang, Raymond Y., et al., "Heterozygous Fabry women are not just carriers, but have a significant burden of disease and impaired quality of life", Genet Med 2007:9(1):34-45., Oct. 31, 2006.

(56) References Cited

OTHER PUBLICATIONS

Weinberg, "Effect of Shipment, Storage, Anticoagulant, and Cell Separation on Lymphocyte Proliferation Assays for Human Immunodeficiency Virus-Infected Patients", Clin. Diagn. Lab. Immunol. vol. 5 No. 6, 1998, 804-807.
Weinreb, Neal J., et al., "Guidance on the Use of Miglustat for Treating Patients with Type 1 Gaucher Disease", American Journal of Hematology 80, 2005, pp. 223-229.
Welch, et al., "Influence of Molecular and Chemical Chaperones on Protrein Folding", Cell Stress and Chaperones vol. 1 No. 2, 1996, 109-115.
Wustman, et al., "1 14. Pharmacological chaperone therapy for Gaucher disease: Mechanism of action, a survey of responsive mutations and phase 1 clinical trial results", Molecular Genetics and Metabolism, 93(2):44 (2008).
Yam, Gary Hin-Fai, et al., "A synthetic chaperone corrects the trafficking defect and disease phenotype in a protein misfolding disorder", The FASB Journal, 2004, 12-18.
Yam, Gary Hin-Fai, et al., "Pharmacological chaperone corrects lysosomal stroage in Fabry disease caused by trafficking-incompetent variants", Am. J. Physiol. Cell Physiol. vol. 290, Apr. 2006, C1076-C1082.
Yam, Gary Hin-Fai, et al., "Sodium 4-Phenylbutyrate Acts as a Chemical Chaperone on Misfolded Myocilin to Rescue Cells from Endoplasmic Reticulum Stress and Apoptosis", Investigative Ophthalmology & Visual Science, Apr. 2007, vol. 48, No. 4, Jan. 29, 2007., 1683-1690.

\* cited by examiner

METHODS FOR TREATMENT OF FABRY DISEASE

CROSS REFERENCE TO RELATED APPLICATIONS

This application is a continuation application of U.S. patent application Ser. No. 15/974,222, filed May 8, 2018, which is a continuation application of U.S. patent application Ser. No. 15/338,923, filed Oct. 31, 2016 (granted as U.S. Pat. No. 9,987,263), which is a continuation application of U.S. patent application Ser. No. 14/641,707, filed Mar. 9, 2015 (granted as U.S. Pat. No. 9,480,682), which is a continuation application of U.S. patent application Ser. No. 13/445,338, filed Apr. 12, 2012 (granted as U.S. Pat. No. 9,000,011), which is a continuation application of U.S. patent application Ser. No. 12/966,904, filed on Dec. 13, 2010 (now abandoned), which is a divisional application of U.S. patent application Ser. No. 11/749,512, filed on May 16, 2007 (granted as U.S. Pat. No. 7,851,143), which claims priority from U.S. provisional patent application Ser. No. 60/801,089, filed on May 16, 2006, and from U.S. provisional patent application Ser. No. 60/853,631, filed on Oct. 23, 2006, each of which is incorporated by reference in its entirety herein.

FIELD OF THE INVENTION

The present invention provides methods to determine whether a patient with Fabry disease will benefit from treatment with a specific pharmacological chaperone. The present invention exemplifies two methods, one in vitro and one in vivo, for determining α-galactosidase A responsiveness to a pharmacological chaperone such as 1-deoxygalactonojirimycin in patient cells. The invention also provides a method for diagnosing Fabry disease in patients suspected of having Fabry disease.

BACKGROUND

Fabry disease is a glycosphingolipid (GSL) lysosomal storage disorder resulting from an X-linked inherited deficiency of lysosomal α-galactosidase A (α-GAL), an enzyme responsible for the hydrolysis of terminal α-galactosyl residues from glycosphingolipids (Brady et al. *N Engl J Med.* 1967; 276: 1163-7). A deficiency in the enzyme activity results in a progressive deposition of neutral glycosphingolipids, predominantly globotriaosylceramide (ceramide trihexoside, CTH, GL-3), in cell of Fabry patients. Symptoms can be severe and debilitating, including kidney failure and increased risk of heart attack and stroke. Certain of the mutations cause changes in the amino acid sequence of α-GAL that may result in the production of α-GAL with reduced stability that does not fold into its correct three-dimensional shape. Although α-GAL produced in patient cells often retains the potential for some level of biological activity, the cell's quality control mechanisms recognize and retain misfolded α-GAL in the endoplasmic reticulum, or ER, until it is ultimately moved to another part of the cell for degradation and elimination. Consequently, little or no α-GAL moves to the lysosome, where it normally hydrolyzes GL-3. This leads to accumulation of GL-3 in cells, which is believed to be the cause of the symptoms of Fabry disease. In addition, accumulation of the misfolded α-GAL enzyme in the ER may lead to stress on cells and inflammatory-like responses, which may contribute to cellular dysfunction and disease.

Fabry disease is classified by clinical manifestations into three groups: a classic form with generalized vasculopathy, an atypical variant form with clinical manifestations limited to cardiac tissue, and later-onset disease, which includes female carriers with mild to severe forms of the disease.

The frequency of the classical form of disease is estimated to be about 1:40,000 to 1:60,000 in males, and is reported throughout the world within different ethnic groups. Classically affected males have little or no detectable α-GAL levels and are the most severely affected. The clinical manifestations include angiokeratoma (small, raised reddish-purple blemishes on the skin), acroparesthesias (burning in hands and feet), hypohidrosis (decreased ability to sweat), and characteristic corneal and lenticular opacities (The *Metabolic and Molecular Bases of Inherited Disease,* 8th Edition 2001, Scriver et al., ed., pp. 3733-3774, McGraw-Hill, New York). Lipid storage may lead to impaired arterial circulation and increased risk of heart attack or stroke. The heart may also become enlarged and the kidneys may become progressively involved. Other symptoms include fever and gastrointestinal difficulties, particularly after eating. The affected male's life expectancy is reduced, and death usually occurs in the fourth or fifth decade as a result of vascular disease of the heart, brain, and/or kidneys.

Individuals with later-onset Fabry disease can be male or female. Late-onset Fabry disease presents as the atypical variant form, and growing evidence indicates there may be a significant number of "atypical variants" which are unaccounted for in the world. Females, who inherit an X chromosome containing an α-GAL mutation, may exhibit symptoms later in life, significantly increasing the prevalence of this disease. These patients typically first experience disease symptoms in adulthood, and often have disease symptoms focused on a single organ. For example, many males and females with later-onset Fabry disease have enlargement of the left ventricle of the heart. Later-onset Fabry disease may also present in the form of strokes of unknown cause. As the patients advance in age, the cardiac complications of the disease progress, and can lead to death.

In contrast, patients with the milder "cardiac variant" of Fabry diseasenormally have 5-15% of normal α-GAL activity, and present with left ventricular hypertrophy or a cardiomyopathy. These cardiac variant patients remain essentially asymptomatic when their classically affected counterparts are severely compromised. Cardiac variants were found in 11% of adult male patients with unexplained left ventricular hypertrophic cardiomyopathy, suggesting that Fabry disease may be more frequent than previously estimated (Nakao et al., *N. Engl. J. Med.* 1995; 333: 288-293).

The α-GAL gene has been mapped to Xq22 (Bishop et al., *Am. J Hum. Genet.* 1985; 37: A144), and the full-length cDNA and entire 12-kb genomic sequences encoding α-GAL have been reported (Calhoun et al., *Proc. Natl. Acad. Sci. USA.* 1985; 82: 7364-7368; Bishop et al., *Proc. Natl. Acad. Sci. USA.* 1986; 83: 4859-4863; Tsuji et al., *Eur. J. Biochem.* 1987; 165: 275-280; and Kornreich et al., *Nucleic Acids Res.* 1989; 17: 3301-3302). There is a marked genetic heterogeneity of mutations that cause Fabry disease (*The Metabolic and Molecular Bases of Inherited Disease,* 8th Edition 2001, Scriver et al., ed., pp. 3733-3774, McGraw-Hill, New York; Eng et al., *Am. J Hum. Genet.* 1993; 53: 1186-1197; Eng et al., *Mol. Med.* 1997; 3: 174-182; and Davies et al., *Eur. J. Hum. Genet.* 1996; 4: 219-224). To date, a variety of missense, nonsense, and splicing mutations, in addition to small deletions and insertions, and larger gene rearrangements, have been reported, although the majority of mutations are missense mutations.

Fabry disease is heterogeneous and it is often difficult to correlate genotype with phenotype. People with the same genotype often exhibit different clinical symptoms and disease pathology. However, there appears to be a correlation between residual enzyme activity and disease severity, with the lower the α-GAL activity resulting in the greatest severity of disease. Although the vast majority of α-GAL mutations are missense mutations, with most being outside the catalytic site, it difficult to predict which mutations result in an unstable enzyme that could be "rescued" by a specific pharmacological chaperone (SPC) which stabilizes the enzyme, and which ones cannot be stabilized using a SPC.

Diagnosis of Fabry Disease

Because Fabry disease is rare, involves multiple organs, has a wide age range of onset, and is heterogeneous, proper diagnosis is a challenge. Awareness is low among health care professionals and misdiagnoses are frequent. Some examples of diagnoses seriously considered in patients who were eventually diagnosed with Fabry's disease include: mitral valve prolapse, glomerulonephritis, idiopathic proteinuria, systemic lupus erythematosus, Whipple's disease, acute abdomen, ulcerative colitis, acute intermittent porphyrias, and occult malignancies. Thus, even for classically affected males, diagnosis typically takes from about 5-7 years or even longer. This is a concern because the longer a person has Fabry disease, the more damage is likely to occur in the affected organs and tissues and the more serious the person's condition may become. Diagnosis of Fabry disease is most often confirmed on the basis of decreased α-GAL activity in plasma or peripheral leukocytes (WBCs) once a patient is symptomatic, coupled with mutational analysis. In females, diagnosis is even more challenging since the enzymatic identification of carrier females is less reliable due to random X-chromosomal inactivation in some cells of carriers. For example, some obligate carriers (daughters of classically affected males) have α-GAL enzyme activities ranging from normal to very low activities. Since carriers can have normal α-GAL enzyme activity in leukocytes, only the identification of an α-GAL mutation by genetic testing provides precise carrier identification and/or diagnosis.

Treatment of Fabry Disease

The only approved therapy for treating Fabry disease diseases is enzyme replacement therapy, which typically involves intravenous, infusion of a purified form of the corresponding wild-type protein (Fabrazyme®, Genzyme Corp.). One of the main complications with protein replacement therapy is attainment and maintenance of therapeutically effective amounts of protein in vivo due to rapid degradation of the infused protein. The current approach to overcome this problem is to perform numerous costly high dose infusions.

Protein replacement therapy has several additional caveats, such as difficulties with large-scale generation, purification, and storage of properly folded protein; obtaining glycosylated native protein; generation of an anti-protein immune response; and inability of protein to cross the blood-brain barrier to mitigate central nervous system pathologies (i.e., low bioavailability). In addition, replacement enzyme cannot penetrate the heart or kidney in sufficient amounts to reduce substrate accumulation in the renal podocytes or cardiac myocytes, which figure prominently in Fabry pathology.

Gene therapy using recombinant vectors containing nucleic acid sequences that encode a functional protein, or using genetically modified human cells that express a functional protein, is also being evaluated to treat protein deficiencies and other disorders that benefit from protein replacement. Although promising, this approach is also limited by technical difficulties such as the inability of vectors to infect or transduce dividing cells, low expression of the target gene, and regulation of expression once the gene is delivered.

A third, relatively recent approach to treating some enzyme deficiencies involves the use of small molecule inhibitors to reduce production of the natural substrate of deficient enzyme proteins, thereby ameliorating the pathology. This "substrate reduction" approach has been specifically described for a class of about 40 related enzyme disorders called lysosomal storage disorders that include glycosphingolipid storage disorders. The small molecule inhibitors proposed for use as therapy are specific for inhibiting the enzymes involved in synthesis of glycolipids, reducing the amount of cellular glycolipid that needs to be broken down by the deficient enzyme. This approach is also limited in that glycolipids are necessary for biological function, especially neurological function, and excessive deprivation may cause adverse effects.

It has previously been shown that the binding of small molecule inhibitors of enzymes associated with LSDs can increase the stability of both mutant enzyme and the corresponding wild-type enzyme (see U.S. Pat. Nos. 6,274,597; 6,583,158; 6,589,964; 6,599,919; 6,916,829, and 7,141,582 all incorporated herein by reference). In particular, it was discovered that administration of small molecule derivatives of glucose and galactose, which are specific, selective competitive inhibitors for several target lysosomal enzymes, effectively increased the stability of the enzymes in cells in vitro and, thus, increased trafficking of the enzymes to the lysosome. Thus, by increasing the amount of enzyme in the lysosome, hydrolysis of the enzyme substrates is expected to increase. The original theory behind this strategy was as follows: since the mutant enzyme protein is unstable in the ER (Ishii et al., *Biochem. Biophys. Res. Comm.* 1996; 220: 812-815), the enzyme protein is retarded in the normal transport pathway (ER→Golgi apparatus→endosomes-→lysosome) and prematurely degraded. Therefore, a compound which binds to and increases the stability of a mutant enzyme, may serve as a "chaperone" for the enzyme and increase the amount that can exit the ER and move to the lysosomes. In addition, because the folding and trafficking of some wild-type proteins is incomplete, with up to 70% of some wild-type proteins being degraded in some instances prior to reaching their final cellular location, the chaperones can be used to stabilize wild-type enzymes and increase the amount of enzyme which can exit the ER and be trafficked to lysosomes. This strategy has been shown to increase several lysosomal enzymes in vitro and in vivo, including β-glucocerebrosidase and α-glucosidase, deficiencies of which are associated with Gaucher and Pompe disease, respectively.

However, as indicated above, successful candidates for SPC therapy must have a mutation which results in the production of an enzyme that has the potential to be stabilized and folded into a conformation that permits trafficking out of the ER. Mutations which severely truncate the enzyme, such as nonsense mutations, or mutations in the catalytic domain which prevent binding of the chaperone, will not likely be "rescuable" or "enhanceable" using SPC therapy. While missense mutations outside the catalytic site are more likely to be rescuable using SPCs, there is no guarantee, necessitating screening for responsive mutations. This means that, even when Fabry disease is diagnosed by detecting deficient α-GAL activity in WBCs, it is very difficult, if not impossible, to predict whether a particular Fabry patient will respond to treatment with an SPC. Moreover, since WBCs only survive for a short period of time in culture (in vitro), screening for SPC enhancement of α-GAL is difficult.

In order to apply SPC therapy effectively, a broadly applicable, fast and efficient method for screening patients for responsiveness to SPC therapy needs to be adopted prior to initiation of treatment. Thus, there remains in the art a need for relatively non-invasive methods to rapidly assess enzyme enhancement with potential therapies prior to making treatment decisions, for both cost and emotional benefits to the patient.

SUMMARY OF THE INVENTION

The present invention provides two methods for determining whether a patient will be a candidate for SPC therapy. Specifically, the present invention provides in vitro and in vivo assays to evaluate α-GAL activity in blood cells derived from patients with Fabry disease in the presence or absence of an SPC. The present invention also includes the basis for evaluation of SPC as a treatment option for any number of other protein abnormalities and/or enzyme deficiencies. The present invention also provides for diagnostic kits containing the components required to perform the assay. The present invention further provides an improved method of diagnosing Fabry disease by determining α-GAL activity in T cells from patients suspected of having Fabry disease.

DETAILED DESCRIPTION

Figure 1:
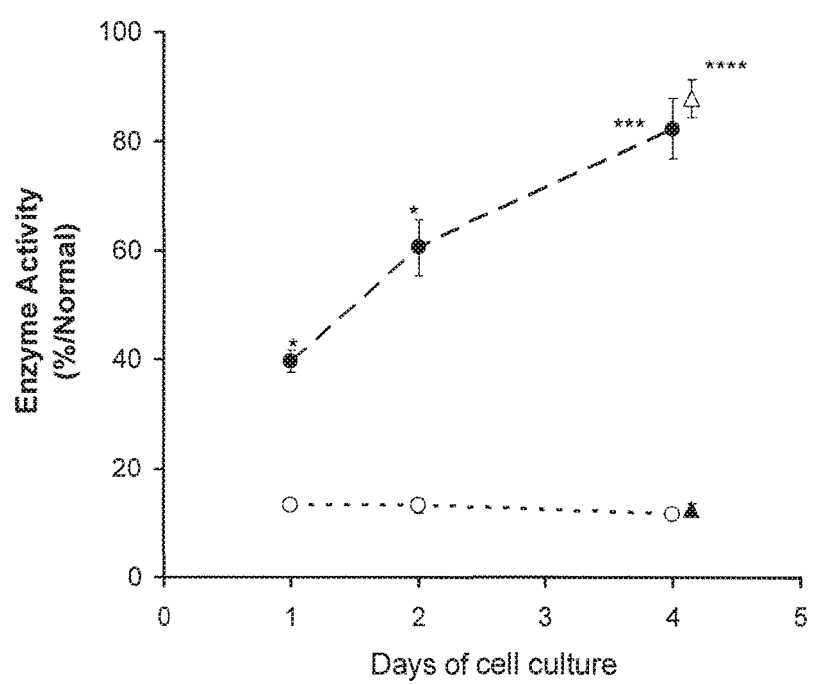
FIG. 1. Time course for enhancement for A97V. T-cells bearing the A97V mutation in α-Gal A were cultured in the absence (open circles) or presence (filled circles) of 20 μM DGJ for one to four days then assayed for α-GAL activity. Changing media after 2 days and replacing with fresh media with (open triangle) or without DGJ (filled triangle) had no effect on the observed enzyme activity.

The present invention provides two assays to allow the accurate determination of whether an SPC enhances enzyme activity from cells derived from patients with Fabry disease. These assays permit a determination of whether the patient will be a candidate for SPC therapy. The new in vitro assay is extremely sensitive and can be performed on isolated T cells which do not need to be extensively cultured and maintained in vivo, which speeds up the time required to perform the assay (as compared to when fibroblasts are used). This assay also can be used as a diagnostic assay for patients suspected of having Fabry disease, especially females, since it is more sensitive than the WBC assay typically used for detecting α-GAL activity. The new in vivo assay is similarly non-invasive and provides a very reliable method for determining whether a SPC therapy will be effective in a particular patient. In addition, in conjunction with genotyping, both assays provide a method for determining whether newly discovered α-GAL mutations (such as spontaneous mutations) cause the α-GAL to misfold and, thus potentially would be "rescuable" using SPCs.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Fabry disease" refers to an X-linked inborn error of glycosphingolipid catabolism due to deficient lysosomal α-galactosidase A activity. This defect causes accumulation of globotriaosylceramide (ceramide trihexoside) and related glycosphingolipids in vascular endothelial lysosomes of the heart, kidneys, skin, and other tissues.

The term "atypical Fabry disease" refers to patients with primarily cardiac manifestations of the α-GAL deficiency, namely progressive globotriaosylceramide (GL-3) accumulation in myocardial cells that leads to significant enlargement of the heart, particularly the left ventricle.

A "carrier" is a female who has one X chromosome with a defective α-GAL gene and one X chromosome with the normal gene and in whom X chromosome inactivation of the normal allele is present in one or more cell types. A carrier is often afflicted with Fabry disease.

A "patient" refers to a subject who has been diagnosed with a particular disease. The patient may be human or animal. A "Fabry disease patient" refers to an individual who has been diagnosed with Fabry disease and has a mutated α-GAL as defined further below. Characteristic markers of Fabry disease can occur in male hemizygotes and female carriers with the same prevalence, although females typically are less severely affected.

Human α-galactosidase A (α-GAL) refers to an enzyme encoded by the human Gla gene. The human α-GAL enzyme consists of 429 amino acids and is in GenBank Accession No. U78027.

As used herein in one embodiment, the term "mutant α-GAL" includes an α-GAL which has a mutation in the gene encoding α-GAL which results in the inability of the enzyme to achieve a stable conformation under the conditions normally present in the ER. The failure to achieve a stable conformation results in a substantial amount of the enzyme being degraded, rather than being transported to the lysosome. Such a mutation is sometimes called a "conformational mutant."

Non-limiting, exemplary α-GAL mutations associated with Fabry disease which result in unstable α-GAL include L32P; N34S; T41I; M51K; E59K; E66Q; I91T; A97V; R100K; R112C; R112H; F113L; T141L; A143T; G144V; S148N; A156V; L166V; D170V; C172Y; G183D; P205T; Y207C; Y207S; N215S; A228P; S235C; D244N; P259R; N263S; N264A; G272S; S276G; Q279E; Q279K; Q279H; M284T; W287C; I289F; M296I; M296V; L300P; R301Q; V316E; N320Y; G325D; G328A; R342Q; E358A; E358K; R363C; R363H; G370S; and P409A.

As used herein, the term "specific pharmacological chaperone" ("SPC") or "pharmacological chaperone" refers to any molecule including a small molecule, protein, peptide, nucleic acid, carbohydrate, etc. that specifically binds to a protein and has one or more of the following effects: (i) enhances the formation of a stable molecular conformation of the protein; (ii) induces trafficking of the protein from the ER to another cellular location, preferably a native cellular location, i.e., prevents ER-associated degradation of the protein; (iii) prevents aggregation of misfolded proteins; and/or (iv) restores or enhances at least partial wild-type function and/or activity to the protein. A compound that specifically binds to e.g., α-GAL, means that it binds to and exerts a chaperone effect on α-GAL and not a generic group of related or unrelated enzymes. More specifically, this term does not refer to endogenous chaperones, such as BiP, or to non-specific agents which have demonstrated non-specific chaperone activity against various proteins, such as glycerol, DMSO or deuterated water, i.e., chemical chaperones (see Welch et al., *Cell Stress and Chaperones* 1996; 1(2):109-115; Welch et al., *Journal of Bioenergetics and Biomembranes* 1997; 29(5):491-502; U.S. Pat. Nos. 5,900,360; 6,270,954; and 6,541,195). In the present invention, the SPC may be a reversible competitive inhibitor.

A "competitive inhibitor" of an enzyme can refer to a compound which structurally resembles the chemical structure and molecular geometry of the enzyme substrate to bind the enzyme in approximately the same location as the substrate. Thus, the inhibitor competes for the same active site as the substrate molecule, thus increasing the Km. Competitive inhibition is usually reversible if sufficient substrate molecules are available to displace the inhibitor, i.e., competitive inhibitors can bind reversibly. Therefore, the amount of enzyme inhibition depends upon the inhibitor concentration, substrate concentration, and the relative affinities of the inhibitor and substrate for the active site.

Following is a description of some specific pharmacological chaperones contemplated by this invention:

1-deoxygalactonojirimycin refers to a compound having the following structures:

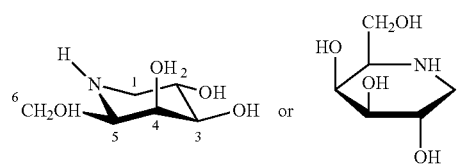

This term includes both the free base and any salt forms. The hydrochloride salt of DGJ is known as migalastat hydrochloride (Migalastat).

Still other SPCs for α-GAL are described in U.S. Pat. Nos. 6,274,597, 6,774,135, and 6,599,919 to Fan et al., and include α-3,4-di-epi-homonojirimycin, 4-epi-fagomine, and α-allo-homonojirimycin, N-methyl-deoxygalactonojirimycin, β-1-C-butyl-deoxygalactonojirimycin, and α-galacto-homonojirimycin, calystegine $A_3$, calystegine $B_2$, calystegine $B_3$, N-methyl-calystegine $A_3$, N-methyl-calystegine $B_2$ and N-methyl-calystegine $B_3$.

As used herein, the term "specifically binds" refers to the interaction of a pharmacological chaperone with a protein such as α-GAL, specifically, an interaction with amino acid residues of the protein that directly participate in contacting the pharmacological chaperone. A pharmacological chaperone specifically binds a target protein, e.g., α-GAL, to exert a chaperone effect on α-GAL and not a generic group of related or unrelated proteins. The amino acid residues of a protein that interact with any given pharmacological chaperone may or may not be within the protein's "active site." Specific binding can be evaluated through routine binding assays or through structural studies, e.g., co-crystallization, NMR, and the like. The active site for α-GAL is the substrate binding site.

"Deficient α-GAL activity" refers to α-GAL activity in cells from a patient which is below the normal range as compared (using the same methods) to the activity in normal individuals not having or suspected of having Fabry or any other disease (especially a blood disease).

As used herein, the terms "enhance α-GAL activity" or "increase α-GAL activity" refer to increasing the amount of α-GAL that adopts a stable conformation in a cell contacted with a pharmacological chaperone specific for the α-GAL, relative to the amount in a cell (preferably of the same cell-type or the same cell, e.g., at an earlier time) not contacted with the pharmacological chaperone specific for the α-GAL. This term also refers to increasing the trafficking of α-GAL to the lysosome in a cell contacted with a pharmacological chaperone specific for the α-GAL, relative to the trafficking of α-GAL not contacted with the pharmacological chaperone specific for the protein. These terms refer to both wild-type and mutant α-GAL. In one embodiment, the increase in the amount of α-GAL in the cell is measured by measuring the hydrolysis of an artificial substrate in lysates from cells that have been treated with the SPC. An increase in hydrolysis is indicative of increased α-GAL activity.

The term "α-GAL activity" refers to the normal physiological function of a wild-type α-GAL in a cell. For example, α-GAL activity includes hydrolysis of GL-3.

A "responder" is an individual (diagnosed with or suspected of having Fabry disease) whose cells exhibit sufficiently increased α-GAL activity, and/or amelioration of symptoms or improvement in surrogate markers, in response to contact with an SPC. Non-limiting examples of improvements in surrogate markers for Fabry disease include increases in α-GAL levels or activity in cells (e.g., fibroblasts) and tissue; reductions in of GL-3 accumulation; decreased plasma concentrations of homocysteine and vascular cell adhesion molecule-1 (VCAM-1); decreased GL-3 accumulation within myocardial cells and valvular fibrocytes; reduction in cardiac hypertrophy (especially of the left ventricle), amelioration of valvular insufficiency, and arrhythmias; amelioration of proteinuria; decreased urinary concentrations of lipids such as CTH, lactosylceramide, ceramide, and increased urinary concentrations of glucosylceramide and sphingomyelin (Fuller et al., *Clinical Chemistry*. 2005; 51: 688-694); the absence of laminated inclusion bodies (Zebra bodies) in glomerular epithelial cells; improvements in renal function; mitigation of hypohidrosis; the absence of angiokeratomas; and improvements hearing abnormalities such as high frequency sensorineural hearing loss progressive hearing loss, sudden deafness, or tinnitus. Improvements in neurological symptoms include prevention of transient ischemic attack (TIA) or stroke; and amelioration of neuropathic pain manifesting itself as acroparaesthesia (burning or tingling in extremities).

The dose that achieves one or more of the aforementioned responses is a "therapeutically effective dose."

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an mRNA band on a gel, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acids include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Method

To easily determine whether SPC therapy will be a viable treatment for Fabry patients, including female carriers, simple, non-invasive DGJ rescue assay of α-GAL activity in WBCs, or subsets of WBCs, from Fabry patients was developed.

I. In Vitro Assay

In one embodiment, the diagnostic method of the present invention involves purifying T cells and establishing T cell cultures from blood specimens from Fabry patients (or patients suspected of having Fabry disease). T cell cultures are then treated with or without an SPC, e.g., DGJ, for a sufficient time period to demonstrate enhancement (i.e., increase) of α-GAL activity. The T cells are then lysed, and the lysate is used in an assay to determine enzyme activity. A sufficient increase in α-GAL activity in the lysates from cells treated with the SPC over the activity in the lysates from untreated cells indicates that the patient will likely respond to SPC therapy (i.e., the patient will be a "responder").

This embodiment can be carried out as follows.

White Blood Cell Separation

The WBCs are prepared using standard techniques, e.g., collection, centrifugation, separation, and washing. More specifically, they can be prepared according to the following steps:

1. A blood sample is drawn from a Fabry patient. In specific embodiments, approximately 8 to 10 mL are drawn into an appropriate container such as a CPT tube from Becton-Dickenson (containing an anti-coagulant and a separation medium).
2. The blood sample is centrifuged to separate red blood cells from white blood cells and plasma. Typically, this step can be performed at room temperature (18-25° C.) at about 1800×g with a tabletop centrifuge for about 20-30 minutes, or until the red blood cells are separated from plasma and white blood cells (WBCs). However, other known white blood cell separation techniques may also be used, e.g., Ficoll-Hypaque, Percoll or other similar density gradients. In an alternative embodiment, T cells are enriched from WBCs using antibody-mediated or magnetic separation using negative selection to remove other cell types in order to obtain unbound T cells. Any known technique for enriching for T cells can be used, although the more expedient, least expensive methods are preferred.
3. Half of the plasma layer is discarded (without disturbing the white blood cell layer) and remaining fluid containing white blood cells is transferred to a centrifuge tube.
4. The WBCs are then pelleted and washed for two or more times by re-suspending the pelleted cells in an appropriate isotonic buffer, e.g., PBS, followed by centrifugation for about 15-20 minutes at about 320×g.

5. The pellet is then re-suspended with a small volume of appropriate isotonic buffer, e.g., PBS. Half of the pellet is transferred to a labeled cryovial for freezing. The other half is used for establishing T cell cultures as described below. The sample that is to be frozen is centrifuged and then resuspended in a small volume of appropriate isotonic buffer, e.g., RPMI 1640 plus DMSO, prior to freezing.

T-Cell Cultures

In one embodiment, T-cell cultures are established by stimulating the T cells present in the WBC preparation, for example, according to the following procedure.
1. The washed cells from above are re-suspended in an appropriate cell culture medium, such as RPMI supplemented with T cell stimulatory cytokines and/or mitogens. Suggested stimulatory cytokines include IL-2, IL-12, IL-15 phytohemagglutinin (PHA), concanavalin A (con A), and pokeweed mitogen. In a particular embodiment, the WBCs are re-suspended in an appropriate volume of RPMI 1640 medium supplemented with FBS, IL-2 and a stimulatory concentration of PHA. They can then be transferred to an appropriate culture vessel and incubated for sufficient time to expand, e.g., about 2-3 days.
2. After the T cells are expanded, they may be frozen, e.g., at about $3 \times 10^6$ cells/vial using RPMI 1640 medium supplemented for cryopreservation, e.g., containing FCS and DMSO. This is sufficient to thaw 5 mL of culture at $5 \times 10^5$ viable cells/mL.

It is noted that one of ordinary skill in the art will be able to ascertain appropriate amounts of T cell stimulatory cytokines or mitogens, although typically such agents are added at amounts from between about 1 ng/ml and about 25 ng/ml (or about 100 U/ml) for cytokines. For mitogens, concentrations range from about 10 ng/ml to about 10 µg/ml for mitogens with most being effective in the low µg/ml range.

Enzyme Activity/Enhancement Assay

Typically, T cells isolated above (e.g., approximately $2.5 \times 10^6$) are grown in culture medium (preceded by thawing if they are frozen), in an appropriate culture vessel in the absence or presence of the SPC, e.g., DGJ, for enough time to evaluate the change in α-GAL activity, e.g., 2 or 3 days. Doses of DGJ expected to enhance α-GAL are in a range from about 2 nM to about 150 µM; preferably about 1 µM to 100 µM, and more preferably about 5 µM to 50 µM. In one specific embodiment, DGJ is added at about 20 µM. Cells can be harvested by centrifugation and washed twice with PBS. Pellets can be stored frozen at −80° C. until assayed for enzyme activity.

Cells are then lysed by the addition of lysis buffer (or deionized water) and physical disruption (pipetting, vortexing and/or agitation, and/or sonication) at room temperature or on ice, followed by pooling of the lysates on ice, then splitting the pooled lysate into small aliquots and freezing.

The lysates can be thawed immediately prior to the assay and should be suspended by use of a vortex mixer and sonicated prior to addition to appropriate wells e.g., in a microplate. N-acetylgalactosamine (GalNAc) is then added to each well (to inhibit α-galactosidase B), followed by a short incubation. 4-methylumbelliferyl-α-D-galactopyranoside (4-MU Gal), or other appropriate labeled DGJ substrate, is then added and the plate is gently mixed for a brief period of time, covered, and incubated at 37° C. for a sufficient time for substrate hydrolysis, usually about 1 hour. To stop the reaction, NaOH-glycine buffer, pH 10.7, is added to each well and the plate is read on a fluorescent plate reader (e.g. Wallac 1420 Victor3™ or similar instrument). Excitation and emission wavelengths were customarily set at 355 nm and 460 nm, respectively. One unit of enzyme activity is defined as the amount of enzyme that catalyzes the hydrolysis of 1 nmole of 4-methylumbelliferone per hour. For each patient sample at least three normal samples should be tested concurrently.

Various modifications of this assay will be readily ascertainable to one of ordinary skill in the art. Examples of artificial substrates that can be used to detect α-GAL activity include but are not limited to p-nitrophenyl-α-D-galactopyranoside and 4-MU GAL. Obviously, only substrates that can be cleaved by human α-GAL are suitable for use. It is noted that while use of a fluorogenic substrate is preferred, other methods of determining α-GAL activity are contemplated for use in the method, including using chromogenic substrates or immunoquantification techniques.

Diagnosis and Prognosis.

The T cell assay can be easily modified for use as a diagnostic assay to diagnose Fabry disease by simply eliminating the step of culturing the T cells in the presence of DGJ prior to performing the enhancement assay. The activity of α-GAL in T cells established from an individual suspected of having Fabry disease can instead be quantitated using T cells from a normal individual as a control. Moreover, both α-GAL activity and SPC enhancement assays can be performed almost simultaneously using the same T cells derived from one patient sample. Since T cells may express more α-GAL (α-GAL in normal T cells as compared with WBCs is much higher), it will be easier to confirm with more certainty whether a patient has α-GAL activity below the normal range because the margin of error will be smaller. Accordingly, use of the T cell assay could potentially prevent misdiagnoses.

In addition, the modified assay also can be used to periodically monitor the progress of patients in whom SPC therapy was initiated to confirm that α-GAL activity remains increased relative to prior to treatment initiation.

II. In Vivo Assay

In a second embodiment, WBCs are evaluated for α-GAL enhancement by an SPC in vivo. In this embodiment, α-GAL activity in WBCs derived from patients is assessed prior to SPC administration, in order to obtain a baseline value. Patients are then administered DGJ daily (e.g., 150 mg/day) for a sufficient time period, e.g., about 10 days to about 2 weeks, followed by extraction of blood and determination of changes in α-GAL activity from the baseline value. Culturing the dells either prior to or following administration is not required.

The dose and dosing regimen of DGJ administration during the in vivo evaluation period may vary depending on the patient since there is so much heterogeneity among mutations, and depending on the patient's residual α-GAL activity. As non-limiting examples, the following doses and regimens are expected to be sufficient to increase α-GAL in most "rescuable" individuals: 25 mg b.i.d; 50 mg once a day; 50 mg b.i.d.; 50 mg once every other day, 75 mg once a day; 75 mg b.i.d.; 100 mg once a day; 100 mg b.i.d.; 150 mg once a day; 150 mg b.i.d., 150 mg once every other day; 250 mg once a day; 250 mg b.i.d. and 250 mg once every other day. In specific embodiments, the doses are 50 mg once a day; 50 mg once every other day; 150 mg once a day; 150 mg once every other day.

Administration of DGJ according to the present invention may be in a formulation suitable for any route of administration, but is preferably administered per os in an oral dosage form such as a tablet, capsule or solution. As one example, the patient is orally administered capsules each containing 25 mg, 50 mg, 75 mg or 100 mg or combinations thereof. For this assay, in the case of oral administration, it is preferred that the patient be administered the DGJ without food (e.g., no food 2 hours before and for 2 hours after dosing) since bioavailability may be lower if taken with food, thereby risking inaccurate results.

Patients who have been on other therapies, such as ERT, should cease treatment for at least about 28 days prior to the in vivo assay to ensure the most accurate results.

White Blood Cell Separation

WBCs are isolated and separated as described above for the T cell in vitro assay. However, no RPMI media or DMSO is to be added to the pellets prior to freezing (as per step 5 above).

Enzyme Activity/Enhancement Assay

Pellets are thawed on ice and cells are then lysed by the addition of lysis buffer and physical disruption (such as by use of a vortex mixer and agitation, and/or sonication at room temperature) for a sufficient time, followed by pooling of the lysates in a polypropylene tube on ice, then splitting of the pooled lysate into aliquots for freezing.

The WBC lysates are then thawed on ice and mixed (again, by sonication and/or vortexing). Samples of each lysate, as well as standards and negative controls, are then added to appropriate wells in e.g., a 24 or 96 well microplate. Equal amounts of GalNAc are added to each well in e.g., citrate/phosphate buffer, pH 4.6, followed by addition of a labeled substrate, such as 4-MU Gal (also in citrate/phosphate buffer, pH 4.6) to all wells, and incubation for a short time at ambient temperature. The plate is then mixed briefly and incubated at 37° C. for a sufficient time period to permit substrate hydrolysis, e.g., about 1 hour. After the sufficient time period, the reaction is stopped by the addition of stop buffer and the plate is read on a fluorescent plate reader (e.g., Wallac 1420 Victor3™) to determine enzyme activity per well.

Various modifications of this assay will be readily ascertainable to one of ordinary skill in the art. Examples of artificial substrates that can be used to detect α-GAL activity include but are not limited to p-nitrophenyl-α-D-galactopyranoside and 4-MU Gal. Obviously, only substrates that can be cleaved by human α-GAL are suitable for use. It is noted that while use of a fluorogenic substrate is preferred, other methods of determining α-GAL activity are contemplated for use in the method, including using chromogenic substrates or immunoquantification techniques.

Eligibility Determination Criteria

The criteria for determining eligibility for SPC therapy depends on the patient's residual enzyme activity at baseline, i.e., the activity determined in the untreated T cells in the in vitro assay, or the activity in the WBCs prior to SPC administration in the in vivo assay. The lower the residual activity, the greater enhancement necessary in order for a patient to be considered a likely responder to treatment.

In one embodiment, the criteria for determining eligibility for the in vitro assay are as follows:

If residual α-Gal A activity in lymphocytes is less than 1% of normal, then α-GAL activity after incubation with DGJ must be at least 2% of normal;

If residual α-GAL activity in lymphocytes is between 1% of normal and <3% of normal, then α-GAL activity after incubation with DGJ must be at least 2× the baseline level;

If residual α-GAL activity in lymphocytes is between 3% of normal and <10% of normal, then α-GAL activity after incubation with DGJ must be at least 3% of normal higher than the baseline level; and If residual α-GAL activity in lymphocytes is 10% of normal or more, then α-GAL activity after incubation with DGJ must be at least 1.3× the baseline level.

In an alternative embodiment, patients with Fabry disease could be categorized as eligible for SPC therapy if their α-GAL activity in T cells in the presence of an SPC such as DGJ is at least about 35-40 nmol/hr/mg protein, which is about 58% of normal. According to the present invention, the average specific was too variable to report as a global mean. Accordingly patient T-cell samples were compared in activity to at least three normal controls collected within 48 h of the collection date for the patient specimen and grown under identical conditions (see Example 1). As a comparison, α-GAL activity in T cells from Fabry patients with the A97V, R301Q, and R111H at baseline was 8 nmole/hr/mg protein, 4 nmol/hr/mg and 1.8 nmol/hr/mg. T cells express higher levels of α-GAL compared with other WBCs, so it is expected that α-GAL activity in a culture enriched for T cells will be significantly higher than what is considered normal in total WBCs (21 nmol/h/mg of protein to about 50 nmol/h/mg of protein; Desnick et al., *The Metabolic and Molecular Bases of Inherited Diseases*. 8th Edition 2001, Scriver et al., ed., pp. 3733-3774, McGraw-Hill, New York). For a comparison, three Fabry patients having the mutations R220X, R356W, and G132R had WBC α-GAL activity of 0.22, 0.18, and 0.26 nmol/hr/mg protein, respectively.

In one embodiment, for the in vivo assay, the following criteria are used to determine eligibility criteria:

If baseline α-GAL is less than 1% of normal, then Day 15 α-GAL activity after treatment with DGJ must be at least 2% of normal;

If baseline α-GAL is between 1% of normal and <5% of normal, then α-GAL activity must be at least 2× the baseline level following the treatment period;

If baseline α-GAL is between 5% of normal and <10% of normal, then α-GAL activity must be at least 5% of normal higher than the baseline level following the treatment period; and If baseline α-GAL is 10% of normal or more, then α-GAL activity must be at least 1.5× the baseline level following the treatment period.

In an alternative embodiment, an increase in activity of at least about 20% in the cells cultured with SPC over the activity in the cells not cultured with SPC, in either the in vitro or in vivo assay, may be indicative that the patient will have a clinically relevant (therapeutically effective) response to SPC therapy.

This discovery provides a method for improving the diagnosis of and facilitating clinical treatment decisions for Fabry disease in particular, and lysosomal storage disease in general. Moreover, this method can be extended to a wide range of genetically defined diseases in appropriate cell types. This class of disease includes the other lysosomal storage disorders, Cystic Fibrosis (CFTR) (respiratory or sweat gland epithelial cells), familial hypercholesterolemia (LDL receptor; LPL-adipocytes or vascular endothelial cells), cancer (p53; PTEN-tumor cells), and amyloidoses (transthyretin) among others.

Kits

The present invention also provides for a commercial diagnostic test kit in order to make therapeutic treatment decisions. The kit provides all materials discussed above and more particularly in, the Examples below, for preparing and running each assay in one convenient package, with the obvious exception of patient blood, optionally including instructions and an analytic guide.

As one non-limiting example, a kit for evaluating α-GAL activity may contain, at a minimum:
  a. at least one T cell stimulatory agent;
  b. a specific pharmacological chaperone;
  c. a chromogenic or fluorogenic substrate for the enzyme assay (including an appropriate standard); and
  d. GalNAc.

The kit may also contain instructions for optimally performing the protein enhancement assay. In another embodiment, the kit will contain the appropriate tubes, buffers (e.g., lysis buffer), and microplates.

In one embodiment, the SPC is supplied in dry form, and will be re-constituted prior to addition.

In another embodiment, the invention provides a kit for the diagnosis of Fabry disease. In this embodiment, the SPC is not included in the kit and the instructions are tailored specifically to diagnosis.

Patients that test positive for enzyme enhancement with an SPC can then be treated with that agent, whereas patients who do not display enzyme enhancement with a specific agent can avoid treatment which will save money and prevent the emotional toll of not responding to a treatment modality.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1: In Vitro Method for Evaluating Effects of an SPC on α-GAL Activity The present Example provides the in vitro diagnostic assay to determine a Fabry patient's responsiveness to a specific pharmacological chaperone.

A. Preparation of Human WBC Pellets for Growth of T Lymphocytes

1. Materials:
CPT tube: Becton-Dickenson (BD Vacutainer® CPT™ Cell Preparation Tube with Sodium Citrate, cat #362761).
Human IL-2 (recombinant), PreProTECH, cat #200-02
Phytohemagglutinin (M Form) (PHA), liquid, Invitrogen, cat #10576-015
RPMI-1640 medium, Mediatech Inc., cat #10-040-CV
Fetal Bovine Serum, Mediatech Inc., cat #35-010-CV
Citric acid, monohydrate, ACS, Mallinckrodt, cat #0627
Sodium phosphate dibasic ($Na_2HPO_4$), ACS, Mallinckrodt cat #7917
Sodium hydroxide, volumetric solution 10N, Mallinckrodt cat #H385
Phosphoric acid, ACS, Mallinckrodt cat #PX0995-3
4-MU α-D-galactopyranoside (4-MU-Gal), Sigma cat #M-7633
N-Acetyl-D-galactosamine (GalNAc), Sigma cat #A-2795
4-methylumbelliferone (4-MU), Sigma cat #M-1381
Glycine, tissue culture grade, Fisher #BP381
Double deionized water
Dulbecco's Phosphate Buffered Saline, PBS, (without Ca, without Mg), Mediatech Inc. cat #21-031-CV
Micro BCA Protein Assay Kit, Pierce cat #23235
96-well microtiter plates, Costar black polystyrene 96 well round bottom, cat #3792
Costar 24-well tissue culture treated microplates, Corning Life Sciences, cat #3526
15 mL polypropylene Falcon tube, Becton Dickinson, cat #352097
Sterile Cryovials
Humidified 5% $CO_2$, 37° C. incubator
37° C. water bath
Fluorescence plate reader 2. WBC Separation:
Patient blood was drawn into an 8 mL CPT tube, which has been stored at 18-25° C.
immediately after collecting blood, it was mixed by inverting the tube 8-10 times.
The tube was centrifuged at room temperature (18-25° C.) for 30 minutes at 1800× g using a tabletop centrifuge equipped with swinging buckets. Universal precautions for handling blood specimens were taken, including the use of a closed canister type bucket for centrifugation.
Following centrifugation, several layers of the blood composition become distinguishable which represented separation of the red blood cells from the plasma and white cells. If this does not occur, warm in hands for 5 minutes and centrifuge again.

3. Washing of WBC's
Half of the plasma layer was aspirated by vacuum and discarded without disturbing the white cell layer. All of the remaining fluid, including the cell layer, was transferred with a Pasteur pipette to a 15 mL conical screw-cap Falcon centrifuge tube.
PBS was added to bring the volume up to 14 mL and the tube was mixed by inversion.
The tube was centrifuged at room temperature for 20-30 minutes at 1300 rpm (approximately 320× g).
Immediately after centrifugation, as much supernatant as possible was aspirated by vacuum and discarded without disturbing the cell pellet.

4. Optional Wash
The cell pellet was re-suspended in the remaining liquid by tapping against the bottom of the tube.
10 mL of PBS was added to the re-suspended cells, and centrifuged at room temperature for 20 minutes at 1300 rpm.
Immediately after centrifugation, as much supernatant as possible was aspirated by vacuum and discarded without disturbing the cell pellet.

5. Optional: Freezing WBC Pellet
The cell pellet was mixed in the remaining liquid by tapping a finger against the bottom of the tube.

0.5 to 1 mL of PBS was added to the re-suspended cells and one half of the pellet was transferred (using a sterile tip on a micropipette) to a labeled 1.8 mL cryovial.

The cryovial was centrifuged at room temperature for 5 minutes at 5000 rpm (approximately 2250 g) in a microcentrifuge.

All of the supernatant liquid was discarded using a Pasteur pipette without disturbing the cell pellet.

0.5 to 1 ml of RPMI 1640 containing 10% FBS and 5% DMSO was then added to the tube and mixed a pipette and frozen overnight at −80 C prior to transferring to a liquid nitrogen cell storage freezer.

B. Establishment of T-Cell Cultures from Blood Specimens
1. The washed cells were re-suspended in 3.0 ml of RPMI 1640 medium with 10% Cosmic Calf Serum (CCS, Hyclone Laboratories, Logan, Utah), about 25 ng/ml IL-2 (PreProTECH, Rocky Hill, N.J.) and the manufacturer's recommended concentration of PHA (Life Technology, Gaithersburg, Md.). The cells were then transferred to an upright an upright 25 cm$^3$ culture flask and incubated for 3-4 days at 37° C., 5% $CO_2$.
2. The cell culture was diluted to 5 ml with growth medium (RPMI-1640, 10% FBS, 25 ng/ml IL-2). The cell concentration was then adjusted to about 5×10$^5$ cells/ml in the flask.
3. The growth of the cells was monitored daily. Cells were maintained between 5×10$^5$ and 1.5×10$^6$ cells in an upright flask. The depth of the medium in the flask did not exceed 1 cm (about 7 mLs in a T25 and 20 mLs in a T75). Cultures can be maintained for approximately 21 days with a doubling time of about 24 hrs. Senescence of the culture will be apparent by a dramatic reduction in growth rate. Culture time may possibly be extended by re-stimulation with PHA.
4. Optional-Freezing T-lymphocytes: T-lymphocytes may be frozen at 3×10$^6$ cells/vial using RPMI1640 medium containing 20% FCS and 7.5% DMSO. On day 5, 6, or 7 cryopreserve as many vials as possible at 3×10$^6$ cells/vial. This is sufficient to thaw 5 mLs of culture at 5×10$^5$ viable cells/ml.

When establishing T-cell cultures, the following should be noted.

Fresh blood specimens should be collected in heparinized tubes (or tubes containing an appropriate anti-coagulant) and used the same day. ACD tubes should be used if specimens cannot be processed within 24 hours. (*Clin Chem* 1988 January; 34(1):110-3; *Clin Diagn Lab Immunol.* 1998 November; 5(6):804-7.).

Eight-10 mLs of blood is usually sufficient to establish 20 million cells by day 5.

T lymphocytes are the specific targets of the HIV virus. Use extreme care if the HIV status of the patient is unknown.

Each new lot of IL-2 should be tested to determine the optimal concentration. The lot from PreProTECH used for these experiments was been found to be optimal at 25 ng/ml with only a slight reduction in cell growth at concentrations up to 50 ng/ml.

Each lot of mitogen, e.g., phytohemagglutinin A (PHA), is assayed by the supplier (Invitrogen) and should be used at the recommended dilution.

All cultures are maintained in a water saturated atmosphere at 37 C, 5% $CO_2$.

Mononuclear cells and lymphocytes may also be collected using either (lymphocyte separation medium (Ficoll-Hypaque) or Lymphoprep tubes following the manufacturer's standard procedure.

When analyzed by fluorescent activated cell sorting, the regimen of IL-2 and PHA stimulation results in 99% CD3-positive cells (which stains all T cell subsets), with equal numbers of CD4-positive and CD4-negative cells (data not shown).

C. Chaperone Treatment

The density of the T cells was adjusted to 1×10$^6$ per 3 ml of culture medium (RPMI-1640, 10% FBS, 25 ng/ml IL-2). 3 ml (~1×10$^6$ cells) are then pipetted into each of 6 wells of a labeled 6-well culture plate and incubated overnight at 37° C., 5% $CO_2$. 3 ml of additional medium was then added to 3 wells to give a final volume of 6 ml/well. To the three remaining wells, 3 ml of medium containing DGJ (Cambridge Major Laboratories, Inc., Germantown, Wis.) at a concentration of about 40 µM (2×; final concentration is 20 µM), for 4-5 days. Cells were harvested by centrifugation (400×g for about 10 minutes) and washed 1× in 10 ml PBS. The resulting pellets were re-suspended in 1 ml PBS and transferred to a 1.7 ml microfuge tube and centrifuged in a refrigerated microfuge at 3000 rpm for 5 minutes. The supernatant was aspirated and the pellets were stored frozen at −80° C. until assayed for enzyme activity.

Note that prior to conducting the enhancement assay, the optimum concentration of DGJ was determined using a range from 2 nM-200 µM. It was determined that 20 µM was optimal.

D. Preparation of Fibroblasts

For a comparison, fibroblast cultures were prepared as described previously (e.g., U.S. Pat. No. 6,274,597). Briefly, fibroblast cultures were derived from skin biopsies of patients and grown in DMEM with 10% FBS until established (3-4 weeks).

E. Activity Assay

Prior to assay, the T cells were thawed on ice and sonicated for 2 minutes, and all other assay reagents were thawed at room temperature. Fluorometric assay of α-GAL activity was performed essentially as described previously (Kusiak et al., *J Biol Chem.* 1978; 253(1), 184-190). The cells were lysed in 0.2 ml deionized water combined with vigorous pipetting and vortexing. The supernatant obtained after centrifugation at 13000 rpm for 2 min at 4° C. was put into a fresh tube and used as the source of α-GAL. α-GAL activity was determined by incubating 50 µl aliquots of the supernatant (containing comparable quantities of protein as determined using 20 µl in a standard protein quantitation assay) in a 24-well microplate at 37° C. with 3.75 mM 4-methylumbelliferyl-α-D-galactopyranoside (4-MU Gal) (Research Products International, Mount Prospect, Ill.) in the citric acid/phosphate buffer (27 mM citrate/46 mM phosphate buffer pH 4.6) without taurocholate and with BSA (3 mg/ml). The percentage of α-GAL was determined by comparing total activity with activity observed in the presence of 117 mM N-acetylgalactosamine (GalNAc) Sigma Chemical Co., St. Louis, Mo.), a specific inhibitor of N-acetylgalactosaminidase. A Wallac 1420 Victor3™ Fluorescence detection reader (Perkin Elmer, CA) was used to measure the released 4-MU at excitation and emission wavelengths of 355 nm and 460 nm, respectively. Appropriate wells for fluorescent standards, and negative (no substrate or no lysate) also were employed. For each patient sample at least three normal samples were tested concurrently.

Incubations were typically 30 minute duration but longer or shorter periods may be employed with similar results.

Enzyme activity (nmol/hr/mg of protein) was calculated according to the following:

$$\frac{\text{Fluorescence of sample}}{\text{Fluorescence of Standard}} * \frac{60 \text{ mins}}{\text{Incubation time (mins)}} *$$

$$\frac{1000 \text{ }\mu L}{\text{Volume assayed }(\mu L)} * \frac{1}{\text{Protein value (mg/mL)}}$$

One unit of enzyme activity is defined as the amount of enzyme that catalyzes the hydrolysis of 1 nmole of 4-methylumbelliferone per hour. The baseline "noise" in the fluorescence output was obtained by evaluating the average of blank six times. If the activity following SPC treatment was at least 2 standard deviations above the baseline, it was considered responsive and not noise.

For the comparative fibroblast enhancement assay, fibroblasts ($\sim$1.5×10$^6$) were grown in 12 ml culture medium in a T75 tissue culture flask in the absence or presence of DGJ at 20 μM for 3 days. At the end of the incubation period, cells were removed from the flask by treatment with trypsin-EDTA solution, collected by centrifugation and washed 3 times with phosphate-buffered saline. Cell pellets were frozen at −80 C until assayed for α-GAL activity. All steps for processing the cell pellet for assay, including the extraction buffer, the time of sonication and the volumes used are the same as used for the T-cells assayed above.

F. Western Blots

The level of α-GAL protein measured by Western blot. Protein was determined using a Micro BCA Protein Assay kit (Pierce, Rockford, Ill.) with bovine serum albumin (BSA) as a standard. Absorbance at 562 nm was measured using the Molecular Devices VersaMax absorbance reader in a 96-well format. For gel electrophoresis prior to western blotting, proteins were separated using Novex Tris-glycine native or SDS-PAGE in 8-16% gradient gels (Invitrogen). Western blots were developed using rabbit polyclonal antibody against α-GAL was performed as described previously (Park et al., *Proc Natl Acad Sci USA*. 2003; 100: 3450-54).

Results

This method described above using T cells is fast and effective when compared with fibroblast-based α-GAL assays conducted substantially similarly to the T cell assay (except that about 1.5×10$^6$ fibroblasts were plated in each well instead of 2.5×10$^6$ T cells).

Using this method, T cells from Fabry patients were incubated without and with 20 μM of DGJ for 1, 2, and 4 days, respectively and the α-GAL activity was measured in cell homogenates and compared to normal control values. When the media was refreshed after 2 days and the cells incubated for 2 additional days, α-GAL activity of A97V was 13% of the normal control (FIG. 1, open circles). However, when 20 μM DGJ was added to the medium of the T cells, the α-GAL activity increased to about 40% of normal after only 1 day of incubation and continued to 80% of normal after 4 days of incubation (FIG. 1, filled circles). Addition of fresh DGJ and media after 2 days and incubation for an additional 2 days did not result in any change in the profile from that observed with a single addition of DGJ. The observed increase in activity after 3 days to a level clearly distinguishable from the α-GAL activity without DGJ led to the adoption of a standard time of measurement after 3 days of incubation with 20 μM of DGJ in subsequent experiments. The use of a three day time course avoids the necessity to provide fresh media and/or splitting the cells after 3 days in culture.

Figure 2A:
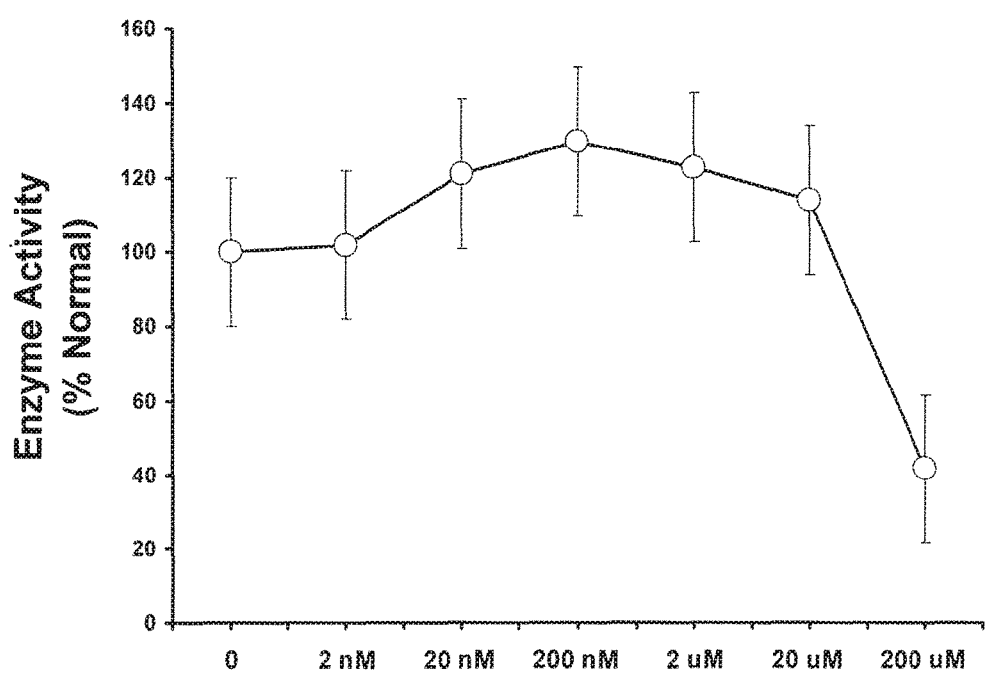
FIG. 2A-C. Concentration Dependence of DGJ in T-cells from normal control and Fabry patients. T-cells from normal individuals (2A) were incubated for 3 days with DGJ from 2 nM to 200 μM then assayed for α-GAL activity. The results of three experiments on different days are shown. T cells from Fabry patients with the A97V (2B), R112H (2C), or R301Q (2C) mutations, respectively, were cultured with DGJ from 2 nM to 200 μM then assayed for α-GAL activity. Three independent sets of DGJ dosage experiments, each of which were performed with triplicate sets are shown.
Figure 2B:
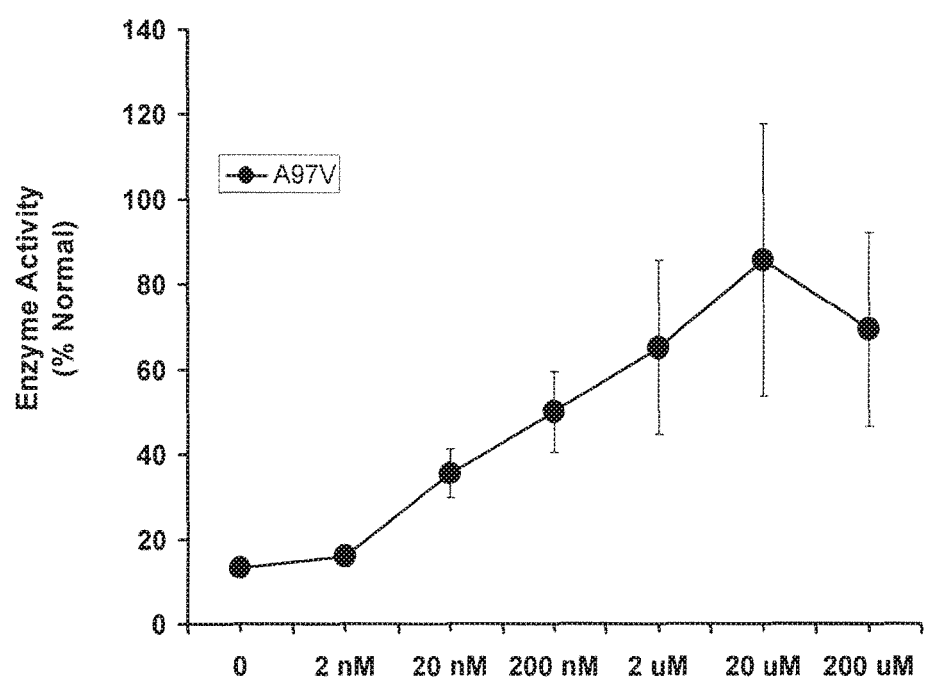
Figure 2C:
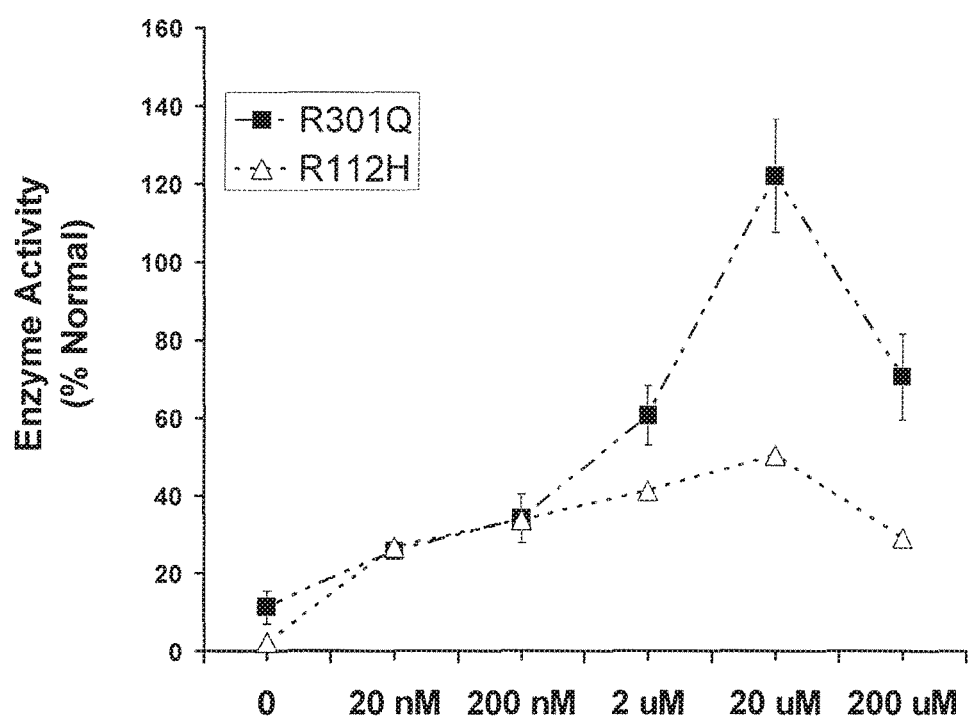

To determine the dosage effect of DGJ in T-cells from normal controls, α-GAL activity was measured in patient cells using a range of DGJ from 2 nM to 200 μM (FIG. 2A) and compared to untreated normal control values assayed on the same day. α-GAL activity increased between 2 nM and 20 μM of DGJ. At 200 μM, DGJ inhibited normal α-GAL activity to approximately 40% of the average of untreated normal controls. The optimal enhancement of mutated α-GAL activity within this same concentration range of DGJ was determined for the A97V mutation and compared with normal controls (FIG. 2B). Three separate experiments were carried out for the dosage effects on A97V. DGJ in concentrations from 2 nM to 20 μM increased the α-GAL activity of A97V in a dose-dependent manner. However, at DGJ concentrations of 200 μM, there was a decrease in α-GAL activity when compared to its highest level when cells were grown in 20 μM DGJ. In all three experiments the optimal enhancement of activity of the A97V mutation was observed at 20 μM DGJ with slightly lower activity at 2 and 200 μM. When the mutations R112H and R301Q were tested in the same concentration range, a similar pattern emerged with the highest level of enhanced activity observed at 20 μM DGJ (FIG. 2C). The results showed various mutations had similar dosage response profiles but different levels of enhancements. Among three α-GAL mutant genotypes tested for the dosage effects, the 20 μM DGJ resulted in an increase in α-GAL to at least 50% of the normal control.

The rescue effect of mutant α-GAL from patients with Fabry disease with at least 11 distinct genotypes has been observed using a pharmacological chaperone using this T cell-based α-GAL assay. Results, presented in Table 1, below, showed that DGJ enhanced the activity of at least five distinct mutant forms of α-GAL in T cells (T) and fibroblasts (F). However, the pharmacological chaperone did not enhance activity of four distinct mutant α-GAL forms. One classical Fabry patient's α-GAL activity was enhanced by DGJ at the intermediate level. The importance of this assay lies in the fact that it can be used to screen for patients who might benefit from pharmacological chaperone administration, thus avoiding the expense and frustration of unnecessary therapy and tissue biopsies.

TABLE 1

| Specimen Number | Patient/ Normal | Sex | Mutation | Number of Replicates (n =) | Activity (% Normal) (−DGJ) | Activity (% Normal) (+DGJ) | Enhancement ratio | Group |
|---|---|---|---|---|---|---|---|---|
| 1 | PT | M | T41I | 3 | 48 | 147 | 3.0 | E |
| 2 | PT | M | T41I | 4 | 61 | 175 | 2.9 | E |
| 3 | PT | M | M51K | 2 | 6 | 29 | 4.6 | E |
| 4 | PT | M | A97V | 3 | 14 | 75 | 5.5 | E |
| 5 | PT | M | R112C | 1 | 10 | 36 | 3.8 | E |
| 6 | PT | M | R112C | 3 | 8 | 49 | 6.3 | E |

TABLE 1-continued

| Specimen Number | Patient/Normal | Sex | Mutation | Number of Replicates (n =) | Activity (% Normal) (−DGJ) | Activity (% Normal) (+DGJ) | Enhancement ratio | Group |
|---|---|---|---|---|---|---|---|---|
| 7 | PT | M | R112H | 2 | 3 | 51 | 15.9 | E |
| 8 | PT | M | R112H | 2 | 8 | 73 | 9.4 | E |
| 9 | PT | M | R112H | 3 | 3 | 60 | 20.0 | E |
| 10 | PT | M | A143T | 4 | 31 | 69 | 2.2 | E |
| 11 | PT | M | A143T | 5 | 49 | 62 | 1.3 | E |
| 12 | PT | M | S201F | 1 | 9 | 82 | 9.6 | E |
| 13 | PT | M | P205T | 1 | 37 | 108 | 2.9 | E |
| 14 | PT | M | N215S | 2 | 15 | 79 | 5.2 | E |
| 15 | PT | M | P259R | 1 | 9 | 297 | 32.6 | E |
| 16 | PT | M | P259R | 3 | 3 | 138 | 47.4 | E |
| 17 | PT | M | F295C | 3 | 1 | 29 | 32.3 | E |
| 18 | PT | M | L300P | 5 | 2 | 72 | 36.1 | E |
| 19 | PT | M | R301Q | 1 | 7 | 91 | 12.3 | E |
| 20 | PT | M | R301Q | 3 | 22 | 204 | 9.1 | E |
| 21 | PT | M | R301Q | 4 | 7 | 80 | 12.1 | E |
| 22 | PT | M | G328A | 4 | 2 | 54 | 24.6 | E |
| 23 | PT | M | R49C | 9 | 3 | 11 | 4.3 | I |
| 24 | PT | M | Y207S | 3 | 4 | 15 | 3.5 | I |
| 25 | PT | M | S276G | 1 | 0 | 9 |  | I |
| 26 | PT | M | S276G | 3 | 1 | 12 | 9.8 | I |
| 27 | PT | M | C94S | 2 | 2 | 2 | NE | NE |
| 28 | PT | M | G128E | 1 | 2 | 4 | NE | NE |
| 29 | PT | M | G128E | 5 | 2 | 2 | NE | NE |
| 30 | PT | M | G132R | 3 | 1 | 2 | NE | NE |
| 31 | PT | M | A143P | 2 | 2 | 1 | NE | NE |
| 32 | PT | M | A143P | 2 | 1 | 1 | NE | NE |
| 33 | PT | M | R220X | 3 | 0 | 1 | NE | NE |
| 34 | PT | M | R227Q | 3 | 4 | 3 | NE | NE |
| 35 | PT | M | W236R | 3 | 1 | 2 | NE | NE |
| 36 | PT | M | G261D | 1 | 0 | 1 | NE | NE |
| 37 | PT | M | G271C | 1 | 2 | 3 | NE | NE |
| 38 | PT | M | G271C | 3 | 1 | 2 | NE | NE |
| 39 | PT | M | N272K | 1 | 0 | 0 | NE | NE |
| 40 | PT | M | W287C | 1 | 1 | 1 | NE | NE |
| 41 | PT | M | W287C | 1 | 1 | 2 | NE | NE |
| 42 | PT | M | R356W | 1 | 1 | 1 | NE | NE |
| 43 | PT | M | R356W | 4 | 0 | 0 | NE | NE |
| 44 | PT | M | dE358 | 3 | 2 | 4 | NE | NE |
| 45 | PT | M | L415P | 1 | 0 | 3 | NE | NE |
| 46 | PT | M | unknown | 1 | 1 | 2 | NE | NE |
| 47 | PT | M | unknown | 2 | 0 | 1 | NE | NE |
| 48 | PT | M | 1042insG | 3 | 1 | 1 | NE | NE |
| 49 | PT | M | 256del1 | 1 | 0 | 0 | NE | NE |
| 50 | PT | M | 30delG | 6 | 2 | 2 | NE | NE |
| 51 | PT | M | 82insG | 2 | 1 | 0 | NE | NE |
| 52 | PT | M | del26bp21 | 1 | 0 | 1 | NE | NE |
| 53 | PT | M | del26bp21 | 1 | 0 | 0 | NE | NE |
| 54 | PT | M | ivs4-1g/a | 2 | 0 | 0 | NE | NE |
| 55 | PT | M | Q119X | 1 | 2 | 1 | NE | NE |
| 56 | PT | M | R220X | 3 | 0 | 1 | NE | NE |
| 57 | PT | M | R301X | 4 | 0 | 7 | NE | NE |
| All NL | NL | M or F |  | 162 | 101 | 128 | 1.3 |  |
| All NL Male | NL | M |  | 115 | 101 | 124 | 1.2 |  |
| All NL Female | NL | F |  | 47 | 84 | 117 | 1.4 |  |
| 58 | NL | F |  | 8 | 120 | 161 | 1.3 |  |
| 59 | NL | F |  | 3 | 88 | 100 | 1.1 |  |
| 60 | NL | F |  | 1 | 95 | 120 | 1.3 |  |
| 61 | NL | F |  | 9 | 85 | 104 | 1.2 |  |
| 62 | NL | F |  | 8 | 103 | 150 | 1.5 |  |
| 63 | NL | F |  | 3 | 107 | 165 | 1.5 |  |
| 64 | NL | F |  | 15 | 106 | 145 | 1.4 |  |
| 65 | NL | M |  | 8 | 100 | 97 | 1.0 |  |
| 66 | NL | M |  | 4 | 80 | 141 | 1.8 |  |
| 67 | NL | M |  | 1 | 172 | 198 | 1.1 |  |
| 68 | NL | M |  | 1 | 271 | 315 | 1.2 |  |
| 69 | NL | M |  | 1 | 110 | 140 | 1.3 |  |
| 70 | NL | M |  | 1 | 101 | 145 | 1.4 |  |
| 71 | NL | M |  | 19 | 106 | 138 | 1.3 |  |
| 72 | NL | M |  | 11 | 90 | 131 | 1.4 |  |
| 73 | NL | M |  | 4 | 75 | 99 | 1.3 |  |
| 74 | NL | M |  | 10 | 105 | 126 | 1.2 |  |
| 75 | NL | M |  | 3 | 97 | 100 | 1.0 |  |

TABLE 1-continued

| Specimen Number | Patient/Normal | Sex | Mutation | Number of Replicates (n =) | Activity (% Normal) (−DGJ) | Activity (% Normal) (+DGJ) | Enhancement ratio | Group |
|---|---|---|---|---|---|---|---|---|
| 76 | NL | M |  | 2 | 93 | 108 | 1.2 |  |
| 77 | NL | M |  | 3 | 85 | 116 | 1.4 |  |
| 78 | NL | M |  | 3 | 89 | 118 | 1.3 |  |
| 79 | NL | M |  | 1 | 127 | 107 | 0.8 |  |
| 80 | NL | M |  | 42 | 100 | 117 | 1.2 |  |
| 81 | NL | M |  | 1 | 102 | 111 | 1.1 |  |

Abbreviations used:
PT: patient;
NL: normal individual;
E: enhanceable;
I: enhanceable (intermediate);
NE: not enhanceable;

It was determined the optimal enhancement of mutated α-GAL activity in the in vitro assay was achieved using about 20 μM DGJ. Among three α-GAL mutant genotypes tested for the dosage effects, the 20 μM DGJ resulted in an increase in α-GAL to at least 50% of the normal control for each (FIG. 3).

In Table 1, the enhanceable group included patients whose α-GAL activity was at least 50% of normal controls when cultured in the presence of DGJ (e.g., R112H was enhanced to 60% of normal control activity). Included in the enhanceable group are the mutations A97V, R301Q, R112H and L300P. For example, the activity of the A97V mutation increased from 14 to 75% of normal in the presence of DGJ, a 6-fold increase. Similarly R301Q increased from 7 to 80% of normal with 12-fold, and R112H increased from 3 to 60%, nearly a 20-fold change. In addition, activity in the L300P mutation was increased from 2% to 72% of normal, a 37-fold increase, which was the highest among the enhanceable mutations examined. L300P was unusual in that some of the activity without DGJ was below the minimum threshold for detection. These results demonstrate mutation-dependent enhancement levels and ratios.

Figure 3:
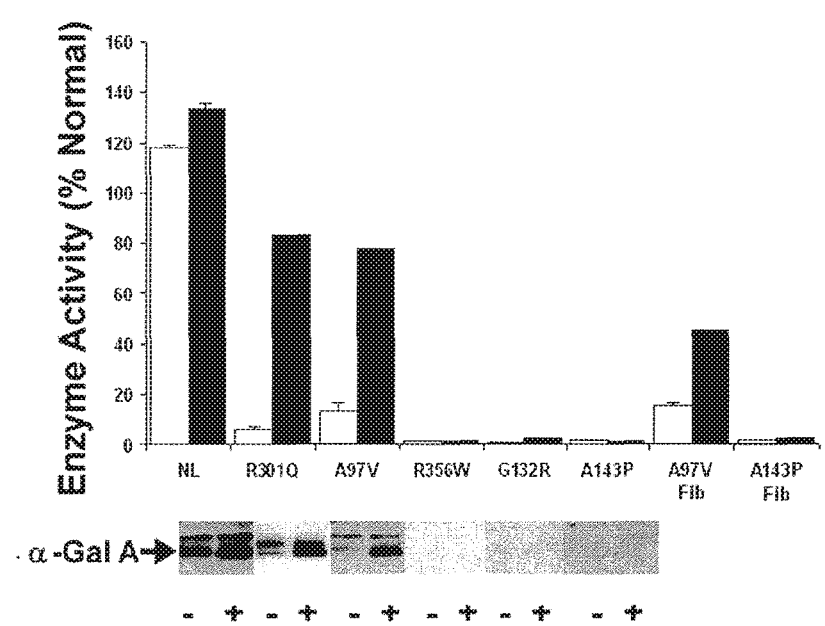
FIG. 3. T-cells from various Fabry patients were cultured in the absence of or in the presence of 20 μM DGJ for three days then assayed for α-GAL activity. Percent of the average normal of specific activity of the α-GAL were graphed to show the effect of DGJ rescue on the different genotypes of Fabry patients. The lower panel shows the Western blot results for each mutation, probed with polyclonal rabbit antibody specific for α-GAL. This demonstrates increased protein stability for enhanceable mutations A97V and R301Q and no increase in protein amount for the mutations R356W, G132R and A143P.

The Western blots showed that the band intensity was considerably increased by treatment with DGJ in normal control cells and those with the A97V and the R301Q mutation, while no increase was seen for R356W, G132R, and A143P (FIG. 3). The protein appears to have shifted to a lower apparent molecular weight indicating maturation of the enzyme by passage from the endoplasmic reticulum, through the Golgi apparatus to the lysosome. The Western blots show that enhancement of α-GAL activity by DGJ is correlated with an increased amount of α-GAL protein. An instance where increased protein levels as measured by Western blots did not result in higher enzyme activity has not yet been observed.

Discussion

The use of T cells in a test system for enhancement of enzymes by SPCs offers significant advantages in the speed of assay and convenience over other culture systems. A critical step in determining which patients may benefit from SPC therapy was the development of a rapid and reliable method for screening of patient-derived cells for enhancement of α-GAL activity by DGJ. The results demonstrate a method for quickly generating a short-lived cell culture that permits the testing of the enhancement and also provides a useful system for future studies on the mechanism of action or for screening of additional chaperone molecules. Leukocytes traditionally used for the diagnosis of affected and carrier status do not survive long enough to permit repeat assays if necessary.

Although Epstein-Barr virus transformed B lymphoblasts (Fan et al., *Nat Med.* 1999; 5(1), 112-115) and primary fibroblast cultures (Fan, supra; Mayes et al., *Clin Chim Acta.* 1981; 112(2), 247-251) have been tested, these are not convenient to use on a large scale for screening of patients for clinical studies. Primary fibroblast cultures require an invasive skin punch biopsy and generally take at least three to four weeks to grow enough cells for the assay. B cell lymphoblasts require Epstein Barr viral transfection and selection process, which is time and labor consuming, in addition to having unknown effects on enzymatic activity.

The present invention provides a method for establishing T cell cultures from fresh blood of normal control individuals and patients with Fabry disease. These cultures can be grown for use in an enhancement assay for α-GAL in 7 to 10 days. These data also show that the effectiveness of DGJ enhancement was evident after about 3 days in the T cell growth media. The data generated are a reproducible measure of the degree of enhanced enzyme activity by a SPC for a specific genotype.

This method can be used for other SPC-based enhancement assays of other genetic diseases including glycosphingolipidoses, mucopolysaccharidoses, and glycogen storage disease (Pompe) and can be extended as a research and clinical protocol in a wide range of genetically defined diseases, such as Cystic Fibrosis (CFTR) and cancer (p53, PTEN), and others.

Example 2: In Vivo Method for Evaluating Effects of an SPC on α-GAL Activity

This example describes results from an open label Phase II study of DGJ in Fabry patients (n=11) with 10 different α-GAL mutations and supports the use of the in vivo assay. The patients were selected for the Phase II study based on the increase in α-GAL activity in the T-cell assay described above. The genotypes were as follows: T41L (2 patients); A143T; A97V; M51K; S276G; L300P; G328A; P205T; N215S; and L415P.

Some patients (8) were administered DGJ according to the following dosing schedule: 25 mg b.i.d. two weeks; 100 mg b.i.d. weeks 2-4; 250 mg b.i.d. weeks 4-6; and 25 mg b.i.d. weeks 6-12. Three patients received 150 mg of DGJ every other day throughout the entire study. Blood was draw into an 8 mL Vacutainer CPT tube at the end of each dosing period and treated as described below.

A. Preparation of Human WBC Pellets for Assay

WBCs were prepared substantially as described in Example 1, with the exception that no FBS/DMSO is added to the pellet prior to freezing.

The preliminary data is summarized in the following table.

B. Preparation of Human WBC Lysates for Assay
- To the microtubes containing the WBC pellet, 0.6 ml of lysis buffer (26 mM citrate/46 mM phosphate, pH 5.5) were added
- Tubes were vortexed until the cells were re-suspended
- Tubes were incubated at room temperature for about 15 minutes, but agitate the suspension by vortexing every couple of minutes
- Tubes were sonicated for 2 minutes, then vortexed for about 10 seconds
- Lysates were incubated on ice until chilled, and then pooled into a pre-chilled polyproylene container (on ice)
- Container was vortexed and pooled lysates were divided into 0.100 mL aliquots in pre-chilled labeled 0.5 mL screw-cap polypropylene microcentrifuge tubes. Pooled lysates were mixed while aliquoting by vortexing between every 10-20 aliquots.
- Aliquots were stored at −80° C. until use.

C. Human WBC Assay
- Each tube containing lysate was thawed on ice, sonicated for 2 minutes, then vortexed for 1 minute.
- 50 µl of each standard, control, or clinical sample was added into appropriate wells of a black polystyrene microplate (use 50 µl of 0.5% BSA in WBC lysis buffer for a standard)
- 50 µl of 117 mM GalNAc was added to all wells, and the plate was incubated for 5 minutes at ambient temperature;
- 50 µl of 5 mM 4-MU Gal substrate was added to to all wells and the wells were mixed on a plate shaker for 30 seconds
- The plate was covered and incubated for about 1 hour at 37° C.
- 100 µl of 0.2M NaOH/Glycine buffer, pH 10.7 was added to each well to stop the reaction
- The plate was read using a fluorescent plate reader as described in Example 1

Results

Figure 4:
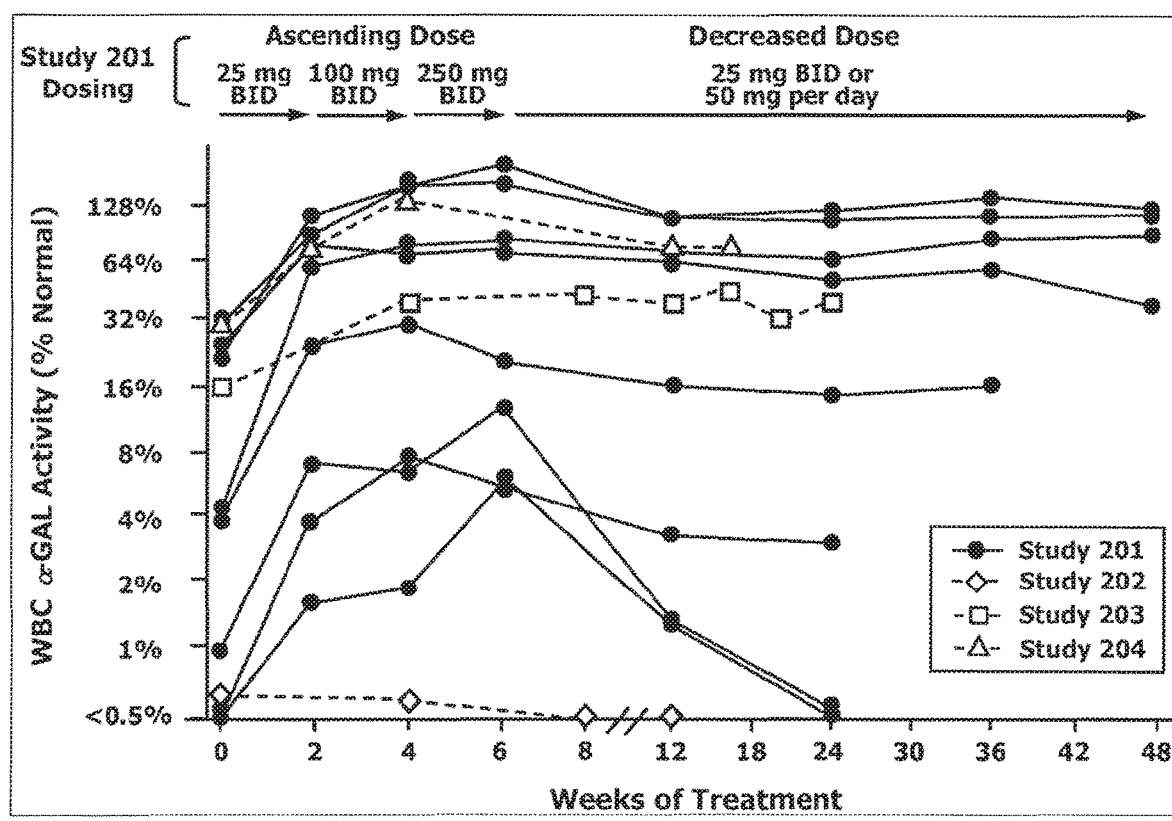
FIG. 4. Graphical representation of in vivo enhancement of α-GAL activity in WBC of Fabry patients following treatment with DGJ.
Figure 5:
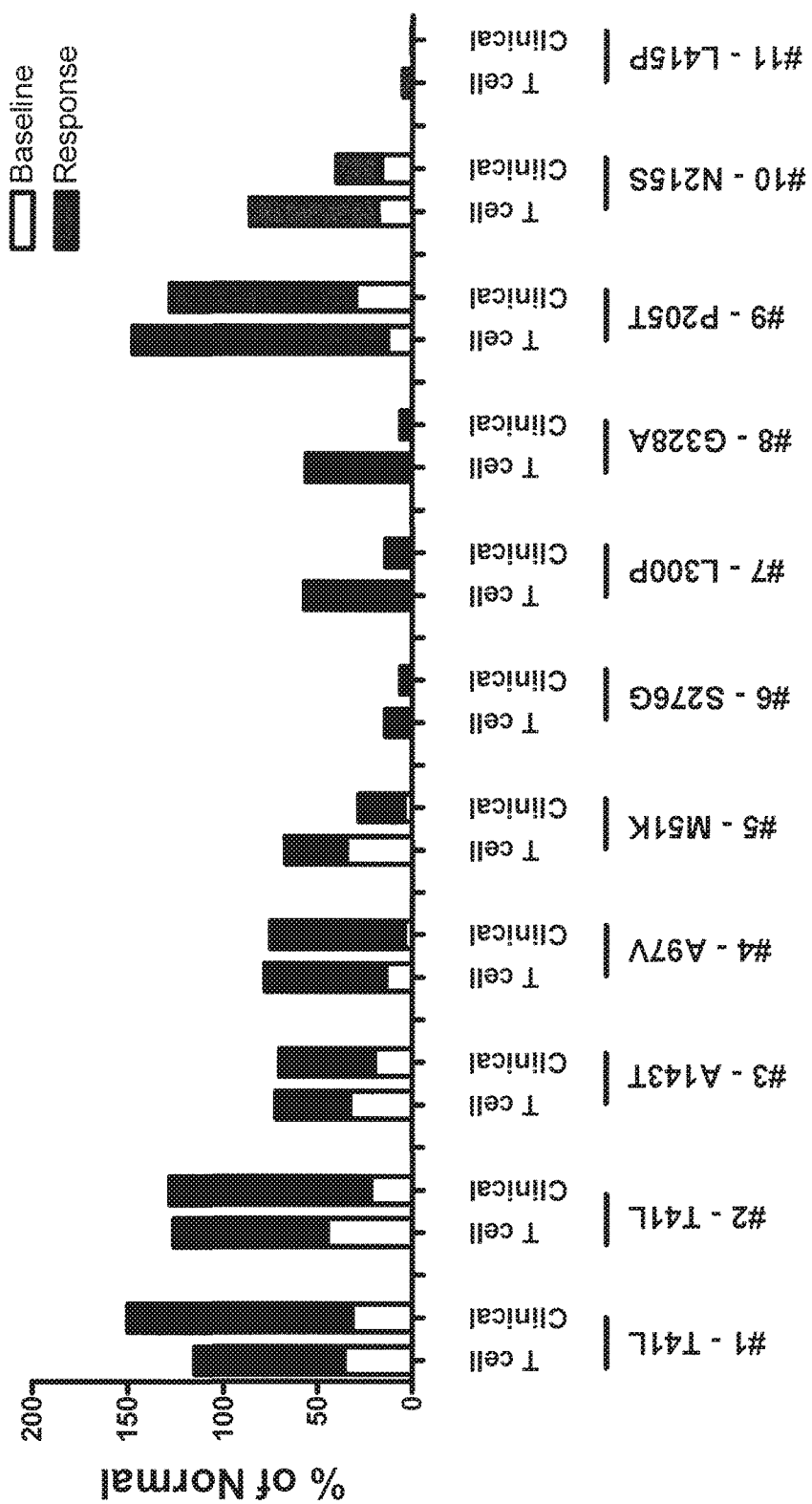
FIG. 5. Graphical representation comparing in vitro and in vivo enhancement of α-GAL activity for 10 genotypes.

The available data from the first eleven patients treated with DGJ for at least 12 weeks suggest that treatment with DGJ leads to an increase in the activity of the enzyme deficient in Fabry disease in 10 of the 11 patients (FIG. 4). The patient with the L415P genotype did not show an increase following DGJ (at 6 weeks) (FIG. 5). For purposes of calculating the percentage of normal in the table, the level of α-GAL that is normal was derived by using the average of the levels of α-GAL in white blood cells of 15 healthy volunteers from the multiple-dose Phase I study. The 11 patients represented 10 different genetic mutations and had baseline levels of α-GAL that ranged from zero to 30% of normal.

The data show an average 2-fold increase in α-GAL activity, and up to 10-fold and 15-fold in some patients as measured in white blood cells. Activity remained elevated from 6-24 weeks and counting when the dose was reduced back to 25 mg b.i.d (data not shown).

Discussion

Based on these results, it appeared possible to screen candidate patients for eligibility for chaperone using an in vivo assay or an in vitro assay using T cells as described in Example 1, since 10 out of 11 patients who demonstrated a significant increase in α-GAL activity in the T cell assay demonstrated an increase following a 2 week treatment with DGJ. Performing an in vivo screen may allow for a more accurate evaluation of the in vivo response to DGJ and other chaperone treatment, since the in vitro assay may not be fully predictive of an in vivo response due to systemic interactions, and may be especially useful to determine appropriate dosing. This dramatic increase in activity appeared after 2 weeks at a low dose of only 50 mg/day (25 mg b.i.d.) (although different dosing regimens are contemplated by the present invention).

These methods can be used for chaperone based enhancement assays for other genetic diseases including glycosphingolipidoses, mucopolysaccharidoses and other lysosomal storage disorders in addition to other genetically based diseases, such as cystic fibrosis where maturation of the protein occurs in the ER.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purpose.

What is claimed is:

1. A method for treatment of Fabry disease in a human patient in need thereof, the method comprising administering to the patient a therapeutically effective dose of 1-deoxygalactonojirimycin or a salt thereof every other day.

2. The method of claim 1, wherein the 1-deoxygalactonojirimycin or salt thereof is administered as an oral dosage form.

3. The method of claim 2, wherein the oral dosage form comprises a tablet, a capsule or a solution.

4. The method of claim 1, wherein the patient does not eat food from about 2 hours before to about 2 hours after administering the 1-deoxygalactonojirimycin or salt thereof.

5. The method of claim 1, wherein the 1-deoxygalactonojirimycin or salt thereof enhances α-galactosidase A activity.

6. The method of claim 1, wherein the patient is male.

7. The method of claim 1, wherein the patient is female.

8. The method of claim 1, wherein the patient has an α-galactosidase A mutation selected from the group consisting of D244N, E59K, F113L, G144V, G183D, G328A, I91T, L32P, M284T, M296V, N263S, R363C, R363H, N34S, T41I, M51K, A97V, R112H, A143T, P205T, Y207S, N215S, P259R, N263S, L300P, E358A, P409A, S201F and F295C.

9. A method for treatment of Fabry disease in a human patient in need thereof, the method comprising administering to the patient a therapeutically effective dose of migalastat hydrochloride every other day.

10. The method of claim 9, wherein the migalastat hydrochloride is administered as an oral dosage form.

11. The method of claim 10, wherein the oral dosage form comprises a tablet, a capsule or a solution.

12. The method of claim 9, wherein the patient does not eat food from about 2 hours before to about 2 hours after administering the migalastat hydrochloride.

13. The method of claim 9, wherein the migalastat hydrochloride enhances α-galactosidase A activity.

14. The method of claim 9, wherein the patient is male.

15. The method of claim 9, wherein the patient is female.

16. The method of claim 9, wherein the patient has an α-galactosidase A mutation selected from the group consisting of D244N, E59K, F113L, G144V, G183D, G328A, I91T, L32P, M284T, M296V, N263S, R363C, R363H, N34S, T41I, M51K, A97V, R112H, A143T, P205T, Y207S, N215S, P259R, N263S, L300P, E358A, P409A, S201F and F295C.

* * * * *